United States Patent
Branch et al.

(10) Patent No.: US 10,261,078 B2
(45) Date of Patent: Apr. 16, 2019

(54) SHEAR HORIZONTAL SURFACE ACOUSTIC WAVE (SH-SAW) RESONATORS AND ARRAYS THEREOF

(71) Applicant: National Technology & Engineering Solutions of Sandia, LLC, Albuquerque, NM (US)

(72) Inventors: Darren W. Branch, Albuquerque, NM (US); Thayne L. Edwards, Bend, OR (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 302 days.

(21) Appl. No.: 15/238,361

(22) Filed: Aug. 16, 2016

(65) Prior Publication Data
US 2017/0052174 A1  Feb. 23, 2017

Related U.S. Application Data

(60) Provisional application No. 62/205,951, filed on Aug. 17, 2015.

(51) Int. Cl.
| | |
|---|---|
| H03H 9/25 | (2006.01) |
| H03H 9/42 | (2006.01) |
| G01N 33/543 | (2006.01) |
| G01N 29/02 | (2006.01) |
| B01L 3/00 | (2006.01) |
| G01N 29/036 | (2006.01) |
| H03H 9/02 | (2006.01) |
| H03H 9/145 | (2006.01) |

(52) U.S. Cl.
CPC .... *G01N 33/5438* (2013.01); *B01L 3/502715* (2013.01); *G01N 29/022* (2013.01); *G01N 29/036* (2013.01); *B01L 2300/0645* (2013.01); *B01L 2300/168* (2013.01); *B01L 2400/0436* (2013.01); *G01N 2291/0255* (2013.01); *G01N 2291/0256* (2013.01); *G01N 2291/0423* (2013.01); *H03H 9/02685* (2013.01); *H03H 9/14552* (2013.01)

(58) Field of Classification Search
CPC ............. G01N 33/5438; G01N 29/022; G01N 29/036; G01N 2291/0255; G01N 2991/0256; G01N 2291/0423; B01L 2300/168; B01L 2400/0436; H03H 9/02685; H03H 9/14552
USPC .......................... 310/313 R, 313 D, 338, 340
See application file for complete search history.

(56) References Cited

U.S. PATENT DOCUMENTS

| 4,837,476 A | 6/1989 | Mochizuki |
|---|---|---|
| 5,073,763 A | 12/1991 | Wright |

(Continued)

OTHER PUBLICATIONS

U.S. Appl. No. 15/239,662, filed Aug. 17, 2016, Branch et al.

(Continued)

*Primary Examiner* — Thomas M Dougherty
(74) *Attorney, Agent, or Firm* — Helen S. Baca

(57) ABSTRACT

The present application relates to a biosensor that employs an acoustic cavity to store mechanical energy. In particular examples, the biosensor includes an electrode region and one or more reflector regions to form the acoustic cavity, as well as a functionalized active area disposed in proximity to the cavity. Methods of making and using such biosensors are also described herein.

25 Claims, 13 Drawing Sheets

(56) References Cited

U.S. PATENT DOCUMENTS

| | | | |
|---|---|---|---|
| 5,914,554 | A | 6/1999 | Kadota et al. |
| 6,127,769 | A | 10/2000 | Kadota et al. |
| 6,293,136 | B1* | 9/2001 | Kim .................... G01N 29/022 310/313 B |
| 6,777,855 | B2 | 8/2004 | Bergmann et al. |
| 6,848,295 | B2 | 2/2005 | Auner et al. |
| 7,053,522 | B1 | 5/2006 | da Cunha |
| 7,173,360 | B2 | 2/2007 | Hartmann et al. |
| 7,500,379 | B2 | 3/2009 | Hines |
| 7,679,474 | B2 | 3/2010 | Igaki et al. |
| 7,878,063 | B1 | 2/2011 | Cular et al. |
| 7,942,568 | B1 | 5/2011 | Branch et al. |
| 8,018,121 | B1 | 9/2011 | Cular et al. |
| 8,425,749 | B1 | 4/2013 | Ravula et al. |
| 8,436,509 | B1 | 5/2013 | Branch |
| 8,525,619 | B1 | 9/2013 | Olsson et al. |
| 8,669,688 | B1 | 3/2014 | Branch |
| 8,709,791 | B1 | 4/2014 | Larson et al. |
| 9,048,807 | B2 | 6/2015 | Pereira Da Cunha et al. |
| 9,276,557 | B1 | 3/2016 | Nordquist et al. |
| 9,337,800 | B1 | 5/2016 | Olsson, III et al. |
| 9,512,421 | B1 | 12/2016 | Branch et al. |
| 2006/0254356 | A1 | 11/2006 | Liu et al. |
| 2006/0283252 | A1 | 12/2006 | Liu et al. |
| 2007/0068256 | A1 | 3/2007 | Xu et al. |
| 2008/0230859 | A1* | 9/2008 | Zaghloul .............. G01N 29/022 257/428 |
| 2009/0272193 | A1* | 11/2009 | Okaguchi ................ G01N 5/02 73/657 |
| 2009/0282902 | A1 | 11/2009 | Warthoe |
| 2010/0075347 | A1 | 3/2010 | Dasaratha et al. |
| 2011/0136262 | A1 | 6/2011 | Ragavan et al. |
| 2015/0111765 | A1 | 4/2015 | Laury-Kleintop et al. |
| 2017/0052174 | A1 | 2/2017 | Branch et al. |
| 2017/0216840 | A1 | 8/2017 | Branch et al. |

OTHER PUBLICATIONS

Auld BA, "Surface Acoustic wave devices," *Arch Acoust.* 1991;16(1):11-30.
Avramov ID et al., "Raleigh SAW resonators using gold electrode structure for gas sensor applications in chemically reactive environments," *Electron. Lett.* 2005;41(7):450-2.
Bisoffi M et al., "Detection of viral bioagents using a shear horizontal surface acoustic wave biosensor," *Biosens Bioelectron.* 2008;23:1397-403.
Branch DW et al., "Love wave acoustic array biosensor platform for autonomous detection," *Ultrasonics Symposium*, held on Oct. 28-31, 2007 in New York, NY (pp. 260-263).
Branch DW et al., "Low-level detection of a Bacillus anthracis simulant using Love-wave biosensors on 36°.YX LiTaO$_3$,", *Biosens. Bioelectron.* Mar. 2004;19(18):849-59.
Branch DW et al., "Shear horizontal surface acoustic wave microsensor for class A viral and bacterial detection," *Sandia Report No. SAND2008-6216*, Oct. 2008 (74 pp.).
Cross PS et al., "Design and applications of two-port SAW resonators on YZ-lithium niobate," *Proc. IEEE* 1976;64(5):682-5.
Cross PS, "Properties of reflective arrays for surface acoustic resonators," *IEEE Trans. Sonics. Ultrason.* 1976;26(4):255-62.
Cross PS, "Reflective arrays for SAW resonators," *Ultrasonics Symposium*, held on Sep. 22-24, 1975, in Los Angeles, CA (pp. 241-244).
Dickert FL et al., "Molecularly imprinted sensor layers for the detection of polycyclic aromatic hydrocarbons in water," *Anal Chem.* 1999;71:4459-63.
Dunnrowics C et al., "Reflection of surface waves from periodic discontinuities," *Ultrasonics Symposium*, held on Sep. 1-Oct. 1, 1976, in Anapolis, MD (pp. 386-390).
Fildes RD et al., "Application of unidirectional transducers to resonator cavities," *Ultrasonics Symposium*, held on Sep. 1-Oct. 1, 1976, in Annapolis, MD (pp. 303-305).

Freudenberg J et al., "A SAW immunosensor for operation in liquid using a SiO$_2$ protective layer," *Sens. Actual. B* 2001;76:147-51.
Gizell E et al., "Sensitivity of the acoustic waveguide biosensor to protein binding as a function of the waveguide properties," *Biosens. Bioelectron.* 2003;18(11):1399-406.
Grate JW et al., "Acoustic wave microsensors: part I." *Anal. Chem.* 1993;65(21):940A-8A.
Grate JW et al., "Acoustic wave microsensors: part II." *Anal. Chem.* 1993;65(22):987A-96A.
Harrington BP et al., "In-plane acoustic reflectors for reducing effective anchor loss in lateral-extension MEMS resonators," *J. Micromech. Microeng.* 2011;21:085021 (11 pp.).
Hashimoto K-Y et al., "Design considerations on surface acoustic wave resonators with significant reflection in interdigital transducers," *IEEE Trans. Ultrason. Ferroelectr. Freq. Control* 2004;51(11):1394-403.
Hohmann S et al., "Surface acoustic wave (SAW) resonators for monitoring conditioning film formation," *Sensors* 2015;15:11873-88.
Krishnamoorthy S, "Development of a ZnO/SiO$_2$/Si high sensitivity interleukin-6 biosensor," *Ph.D. dissertation for the University of Maryland, College Park*, 2007 (168 pp.).
Lakin KM et al., "Planar surface acoustic wave resonators," *Ultrasonic Symposium*, held on Nov. 11-14, 1974, in Milwaukee, WI (pp. 263-267).
Länge K et al., "A surface acoustic wave biosensor concept with low flow cell volumes for label-free detection," *Anal. Chem.* 2003;75:5561-6.
Länge K et al., "Integration of a surface acoustic wave biosensor in a microfluidic polymer chip," *Biosens. Bioelectron.* 2006;22:227-32.
Länge K et al., "Packaging of surface acoustic wave (SAW) based biosensors: an important issue for future biomedical applications," *IEEE International Frequency Control Symposium and Exposition*, held on Aug. 23-27, 2004 in Montreal, Canada (pp. 321-325).
Länge K et al., "Chemical modification of parylene C coatings for SAW biosensors," *Sens. Actual. B* 2007;125:441-6.
Länge K et al., "Surface acoustic wave biosensors: a review," *Anal. Bioanal. Chem.* 2008;391:1509-19.
Li RCM et al., "Surface-wave resonators using grooved reflectors," *29$^{th}$ Annual Symposium on Frequency Control*, held on May 28-30, 1975 in Fort Monmouth, NJ (pp. 167-176).
Malocha DC et al., "A passive wireless multi-sensor SAW technology device and system perspectives," *Sensors* 2013;13:5897-922.
Martin SJ et al., "Characterization of SH acoustic plate mode liquid sensors," *Sens. Actuat.* 1989;20:253-68.
Matthaei GL et al., "A study of the Q and modes of SAW resonators using metal "waffle-iron" and strip arrays," *IEEE Trans. Sonics Ultrason.* 1978;25(3):138-46.
McGill RA et al., "Performance optimization of surface acoustic wave chemical sensors," *IEEE Trans. Ultrason. Ferroelectr. Freq. Control* Sep. 1998;4(5):1370-80.
Md Raiib AA et al., "Piezoelectric thin films for double electrode CMOS MEMS surface acoustic wave (SAW) resonator," *Microsys. Technol.* 2014 (10 pp.) (available at http://link.springer.com/article/10.1007%2Fs00542-014-2319-0).
Morgan D, "Resonators and resonator filters," Chapter 11 in *Surface Acoustic WaveFilters with Applications to Electronic Communications and Signal Processing*, 2007, Elsevier Ltd. (pp. 317-358).
Morgan DP et al., "One-pot SAW resonators using natural SPUDT substrates," *IEEE Trans. Ultrason. Ferroelectr. Freq. Control* Oct. 2007;54(10):1936-42.
Mousavi SA et al., "Design and simulation of one-port SAW resonator for wireless and high temperature application," *IEEE International Conference on Semiconductor Electronics*, held on Nov. 25-27, 2008 in Johor Bahru, Malaysia (pp. 18-22).
Nomura T et al., "Liquid sensing system based on two-port SH-SAW resonator," *Ultrasonics Symposium*, held on Oct. 17-20, 1999 in Tahoe, NV (vol. 1, pp. 477-480).
Nomura T et al., "Liquid sensor probe using reflecting SH-SAW delay line," *Sens. Actuat. B* 2003;91:298-302.

(56) References Cited

OTHER PUBLICATIONS

Nordquist CD et al., "On/Off micro-electromechanical switching of AlN piezoelectric resonators," *IEEE MTT-S International Microwave Symposium Digest*, held on Jun. 2-7, 2013 in Seattle, WA (pp. 1-4).
Patel N et al., "Comparative study of lithium niobate crystal cuts for use as high-voltage acoustic wave sensors," *IEEE Int'l Ultrasonics Symposium*, held on Sep. 3-6, 2014 in Chicago, IL (pp. 1983-1985).
Plessky V et al., "Coupling-of-modes analysis of SAW devices," *Int. J. High Speed Electron Sys.* 2000;10(4):867-94.
Powell DA et al., "Optimum sensitive area of surface acoustic wave resonator chemical and bio-sensors," *IEEE Sensors*. held on Oct. 30-Nov. 3, 2005 in Irvine, CA (pp. 1229-1232).
Rocha Gaso MI, "Analysis. Implementation and validation of a Love mode surface acousitc wave device for its applications as sensor of biological processes in liquid media," *Ph.D. dissertation for the Universitat Politècnica de València*, 2013 (270 pp.).
Rocha Gaso MI et al., "Love wave biosensors: a review." Chapter 11 in *Love Wave Biosensors: A Review, State of the Art in Biosenors—General Aspects*, T. Rinken (ed.), 2013, InTech (pp. 277-310) (available from http://www.intechopen.com/books/state-of-the-art-in-biosensors-general-aspects/love-wave-biosensors-a-review).
Rocha Gaso MI et al., "Surface generated acoustic wave biosensors for the detection of pathogens: a review," *Sensors* 2009;9:5740-69.
Rosenberg RL et al., "Scattering analysis and design of SAW resonator filters," *IEEE Trans. Sonics Ultrason.* 1979;26(3):205-30.
Schmitt RF et al., "Rapid design of SAW oscillator electronics for sensor applications," *Sens. Actuat. B* 2001;76:80-5.
Schweyer MG et al., "Comparison of surface transverse wave (STW) and shear horizontal acoustic plate mode (SHAPM) devices for biochemical sensors," *IEEE International Frequency Control Sysposium*. held on May 28-30, 1997 in Orlando, FL (pp. 147-155).
Shui Y et al., "Optimization of single-phase, unidirectional transducers using three fingers per period," *IEEE Trans. Ultrason. Ferroelectr. Freq. Control* 2002;49(12):1617-21.
Uno T et al., "Optimization of quartz SAW resonator structure with groove grating," *IEEE Trans. Sonics Ultrason.* 1982;29(6):299-310.
Wang W et al., "A Love wave reflective delay line with polymer guiding layer for wireless sensor application," *Sensors* 2008;6:7917-29.
Wang W et al., "Optimal design on SAW sensor for wireless pressure measurement based on reflective delay line," *Sens Actual. B* 2007;139:2-6.
Yantchev V et al., "Micromachines thin film plate acoustic resonators (FPAR): Theory and applications," *24th European Frequency and Time Forum*, held on Apr. 13-16, 2010 in Noordwijk, the Netherlands (pp. 1-8).
Yantchev V et al., "Thin film Lamb wave resonators in frequency control and sensing applications: a review," *J. Micromech. Microeng.* 2013;23:043001 (14 pp.).
Yeo LY et al., "Surface acoustic wave microfluidics," *Annu. Rev. Fluid Mech.* 2014;46:379-406.
International Search Report for International Appl. No. PCT/US17/14962, filed Jan. 25, 2017 (2 pp.).
Written Opinion with Search History for International Appl. No. PCT/US17/14962, filed Jan. 25, 2017 (10 pp.).

\* cited by examiner

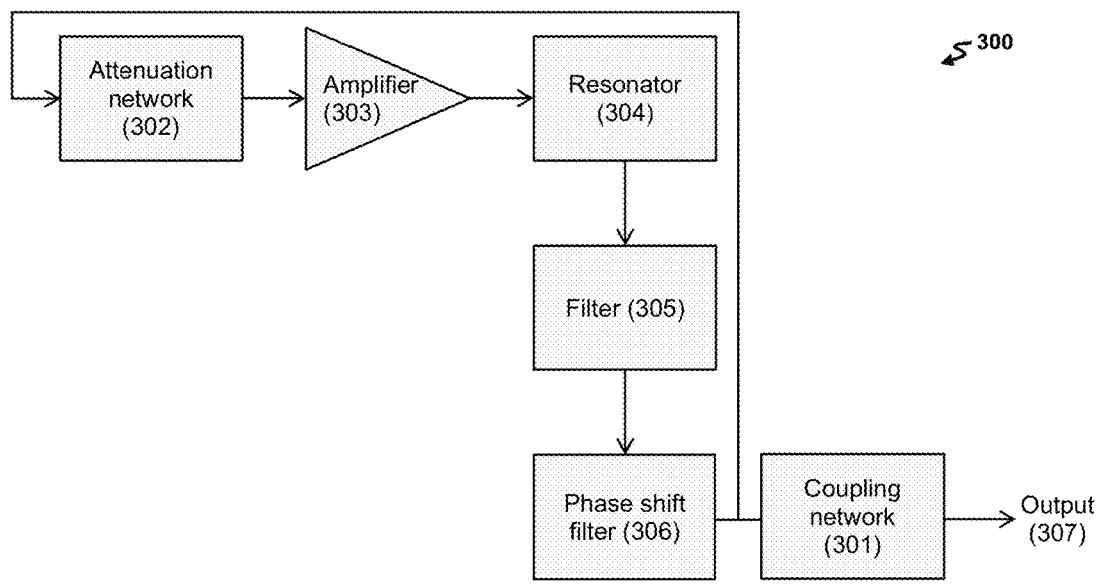
FIG. 3A
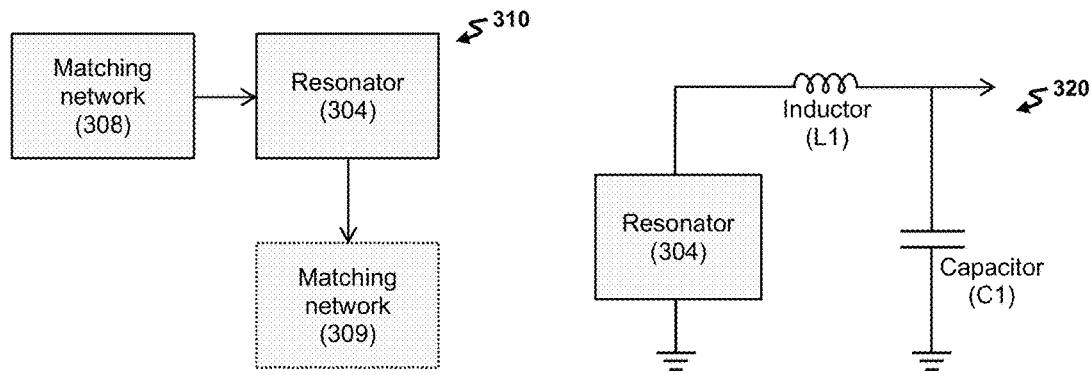
FIG. 3B  FIG. 3C

SHEAR HORIZONTAL SURFACE ACOUSTIC WAVE (SH-SAW) RESONATORS AND ARRAYS THEREOF

CROSS-REFERENCE TO RELATED APPLICATION

This application claims priority to U.S. Provisional Patent Application No. 62/205,951, filed on Aug. 17, 2015 under the title, "SHEAR HORIZONTAL SURFACE ACOUSTIC WAVE (SH-SAW) RESONATORS AND ARRAYS THEREOF," the entirety of which is incorporated herein by reference.

STATEMENT OF GOVERNMENT INTEREST

This invention was made with Government support under contract no. DE-AC04-94AL85000 awarded by the U.S. Department of Energy to Sandia Corporation. The Government has certain rights in the application.

FIELD

The present application relates to a Love wave biosensor that employs an acoustic cavity to store mechanical energy. Methods of making and using such biosensors are also described herein.

BACKGROUND

Acoustic wave-based biosensors can provide a useful platform having high sensitivity and specificity with minimal preparation of the test sample. In particular, acoustic waves can display high sensitivity to changes in mass or viscosity. Specificity can be imparted by surface attachment of a capture agent that specifically binds to the desired target, thereby increasing the mass in vicinity to the acoustic wave. In addition, such platforms can be minimized to allow for field deployable detection systems, as well as simplified for use by non-specialists. On-site detection of contagious or harmful pathogens, immunoassays, virus, bacteria, nucleic acids, DNA, RNA, proteins, or biomarkers would be useful for rapid screening in resource-limited conditions or diagnosing and monitoring of a broad range of targets in healthcare, veterinary, food, water, and environmental testing. There is a need for additional device architectures and platform systems with improved sensitivity, specificity, usability, and/or portability.

SUMMARY

The present application relates to biosensors that employ a particular type of acoustic wave. The acoustic wave is generated and propagated along a piezoelectric substrate, and an electrode region provides the initial electrical field distribution that is required to generate a mechanical acoustic wave within the piezoelectric substrate. When a guide layer is disposed on a surface of the piezoelectric substrate (e.g., in which the shear velocity in the guide layer is less than the shear velocity in the piezoelectric substrate), the surface wave is confined within the guide layer, and the confined wave is characterized as a Love wave. Based on the orientation of the piezoelectric substrate (e.g., a specific cut that is oriented along a particular crystal) and the orientation of the electrode region, particular types of acoustic waves can be generated. In one embodiment, the orientation is such that the surface acoustic wave (SAW) is a shear wave that is horizontally polarized (a shear horizontal wave or SH wave). The wave is shear because the particle displacement of the wave is perpendicular to the wave propagation direction. In addition, the wave is horizontally polarized because the particle displacement of the wave is parallel to a surface of the substrate.

Furthermore, the biosensor can be a resonator that employs an acoustic cavity, in which the generated acoustic wave provides a standing wave within that cavity. The acoustic cavity can be defined in any useful manner (e.g., by use of reflectors, such as Bragg gratings). The cavity stores the mechanical energy from the multi-pass wave. Because acoustic standing waves of the resonator reflect back and forth a plurality of times (e.g., about 100 times or more) through the cavity in the process of achieving resonance, the biosensor has enhanced sensitivity (e.g., a greater sensitivity than a sensor employing a SH-SAW delay-line that lacks the acoustic cavity). The area of the cavity can be minimized, as needed, which in turn minimizes sample use. In some embodiments, the area can be from about 0.01 mm$^2$ to about 10 mm$^2$, such as from 0.01 mm$^2$ to 5 mm$^2$, 0.01 mm$^2$ to 1 mm$^2$, 0.01 mm$^2$ to 0.5 mm$^2$, 0.01 mm$^2$ to 0.1 mm$^2$, 0.05 mm$^2$ to 10 mm$^2$, 0.05 mm$^2$ to 5 mm$^2$, 0.05 mm$^2$ to 1 mm$^2$, 0.05 mm$^2$ to 0.5 mm$^2$, 0.05 mm$^2$ to 0.1 mm$^2$, 0.1 mm$^2$ to 10 mm$^2$, 0.1 mm$^2$ to 5 mm$^2$, 0.1 mm$^2$ to 1 mm$^2$, 0.1 mm$^2$ to 0.5 mm$^2$, 0.5 mm$^2$ to 10 mm$^2$, 0.5 mm$^2$ to 5 mm$^2$, 0.5 mm$^2$ to 1 mm$^2$, 1 mm$^2$ to 10 mm$^2$, or 1 mm$^2$ to 5 mm$^2$. In some embodiments, a sample volume can be reduced to less than about 50 nL, such as from about 0.5 nL to 5 nL, 0.5 nL to 10 nL, 0.5 nL to 25 nL, 0.5 nL to 50 nL, 1 nL to 5 nL, 1 nL to 10 nL, 1 nL to 25 nL, 1 nL to 50 nL, 2 nL to 5 nL, 2 nL to 10 nL, 2 nL to 25 nL, 2 nL to 50 nL, 5 nL to 10 nL, 5 nL to 25 nL, 5 nL to 50 nL, 10 nL to 25 nL, or 10 nL to 50 nL.

Specificity for a particular target can be imparted by capture agents deposited on a surface of the piezoelectric substrate. Binding of a target to the capture agent results in an environmental change (e.g., a mass change) to the cavity, where such binding causes energy loss and decreases the velocity of the acoustic waves. This decrease in velocity then translates to a resonant frequency shift, which can be measured electrically. In this way, changes to the standing waves inside the cavity can be measured using electrical ports. By detecting a change in frequency, the user avoids the limitations from measuring changes in phase, where such limitations include phase wrapping (e.g., where phases changes greater than $2\pi$ cannot be accurately accounted). Due to this mode of detection, the SH-SAW biosensor having a cavity can be monitored in an open loop configuration (e.g., with no feedback and operated as a frequency sweep) or in a closed loop configuration (e.g., with some gain and operated as an oscillator). Such a closed loop circuit would be compact and can be useful for designing a portable platform.

In one particular embodiment, the present application is directed to a shear horizontal surface acoustic wave biosensor including a piezoelectric substrate, an electrode region (e.g., one or more interdigital transducers disposed on the substrate to primarily excite a SH wave in the substrate and to detect the SH wave transmitted through the substrate), one or more reflector regions (e.g., one or more reflector regions configured to provide an acoustic cavity disposed within or on the piezoelectric substrate), a guide layer on the substrate (e.g., a guide layer that has a lower shear velocity than the substrate for confining the SH wave therein as a guided Love wave), and a functionalized active area disposed in proximity to (e.g., above) the acoustic cavity (e.g., where the active area includes one or more capture agents configured to bind one or more targets). In some embodiments, the electrode region includes one or more electrodes configured to launch the guided Love wave through the functionalized active area. In other embodiments, the electrode region includes one or more electrodes configured to detect the guided Love wave that is transmitted through the functionalized active area.

The present application also includes the biosensor (e.g., any described herein) for use with any useful module (e.g., a fluidics module, an electronics module, and/or a control module), any useful circuit (e.g., an oscillation circuit, an impedance matching network, a frequency sweep circuit, etc.), and any useful capture agent (e.g., any described herein). Additional details follow.

Definitions

As used herein, the term "about" means +/−10% of any recited value. As used herein, this term modifies any recited value, range of values, or endpoints of one or more ranges.

By "electrical connection," as used herein, refers to any conductive or semi-conductive structure through which an electrical signal may pass. The electrical signal can be any useful change in electrical field, electric potential, current, or voltage. Non-limiting structures include lines, contact pads, busses, pins, connectors, bond lines, bond pads, etc., formed from any useful material (e.g., an ohmic material, a metal, etc.).

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

As used herein, the terms "top,"0 "bottom," "upper," "lower," "above," and "below" are used to provide a relative relationship between structures. The use of these terms does not indicate or require that a particular structure must be located at a particular location in the apparatus.

Other features and advantages of the application will be apparent from the following description and the claims.

BRIEF DESCRIPTION OF THE DRAWINGS

FIG. 3A-3E shows exemplary electronic modules for use with a biosensor. Provided are schematics of (A) an exemplary circuit 300 for use in a module, (B) an exemplary circuit 310 including impedance matching networks, and (C) an exemplary impedance matching network 320 including a resonator 304 (e.g., any biosensor described herein). Also provided are (D) a Smith chart showing impedance matching by measuring the S11 reflection parameter for a biosensor in use with an impedance matching network and (E) transient data showing the output frequency of a one-port biosensor in use with a monitoring circuit having a Colpitts oscillator circuit, in which the start-up time was about 20 ns and the frequency was about 405.68 MHz.

DETAILED DESCRIPTION

The present application relates to a Love wave biosensor, in which Love waves are generated within the sensor and reflected within a resonator cavity disposed within the sensor. Love waves are guided waves having a shear horizontal (SH) polarization, in which the plane wave polarization (or particle displacement within that wave) is both parallel to the surface of the substrate and perpendicular to the wave propagation direction. Such Love waves require a guide layer disposed above the piezoelectric substrate having a higher shear velocity, thereby allowing Love waves to be trapped and propagated within the guide layer. Without the guide layer, the acoustic wave does not propagate on the surface of the substrate but tends to propagate towards the center of the bulk piezoelectric substrate (or leak into the substrate).

In addition, the biosensor includes an acoustic cavity, which is formed by employing one or more reflector regions. The electrode region can include a transmitting transducer, which launches the acoustic wave by applying an electrical distribution field to a piezoelectric substrate; and the reflection region confines the wave within a cavity. In particular embodiments, the reflection region(s) are disposed outside of a periphery of the electrode region, thereby confining the wave and minimizing loss into the surrounding substrate. The electrode region can further include a receiving transducer, which detects the acoustic wave and transduced the mechanical wave into an electrical signal by inverse piezoelectrical coupling. To bind the desired target, one or more capture agents can be disposed in proximity to the acoustic cavity.

Figure 1A:
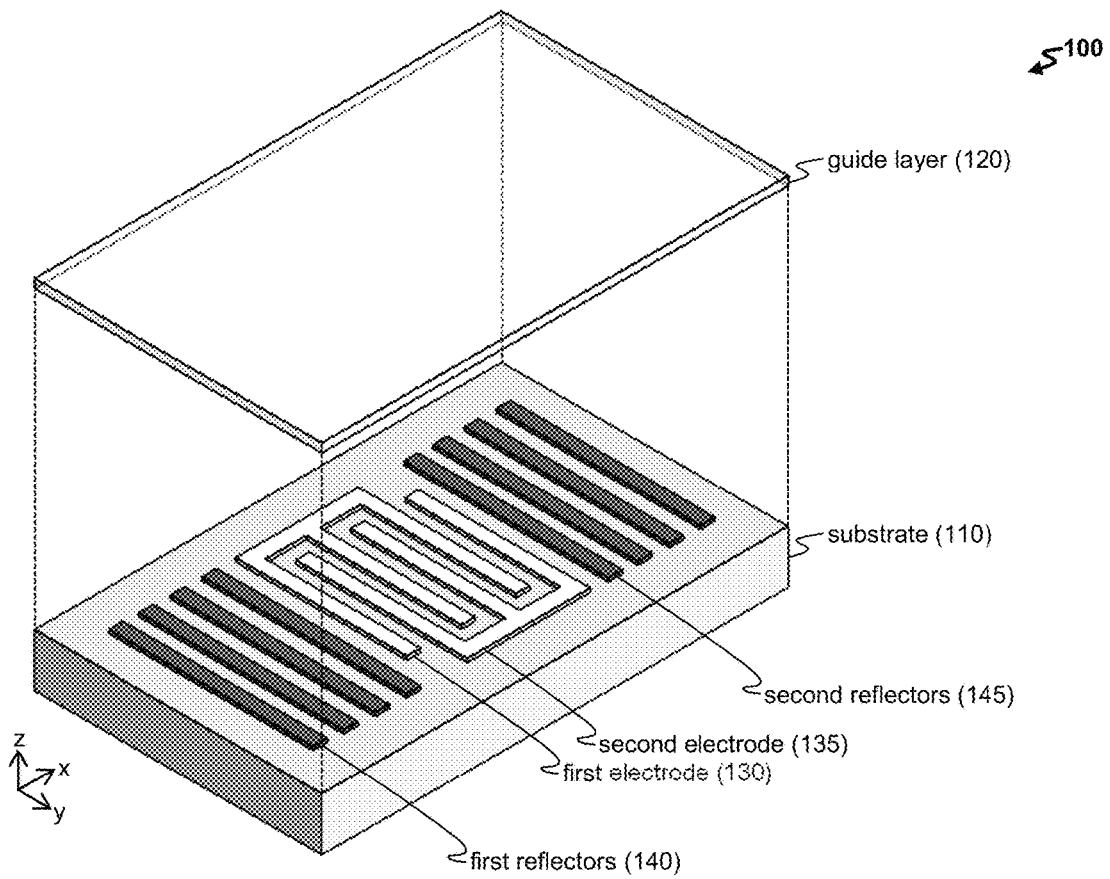
FIG. 1A-1D shows schematics of an exemplary biosensor having various components. Provided are (A) an exemplary one-port biosensor 100 in an exploded view, (B) an assembled biosensor 1000, (C) a cross-sectional view along line 1C-1C in FIG. 1B, and (D) a plan view of the top surface of the biosensor.

FIG. 1A shows an exemplary biosensor 100, which includes a piezoelectric substrate 110 and an electrode region configured to generate and detect acoustic waves. In one exemplary embodiment, the biosensor is configured as a one-port device having a pair of transducers. Each pair includes a transmitting transducer and a receiving transducer, in which the transmitting transducer is an active electrode configured to provide an electrical field and the receiving transducer is a grounded electrode configured to transduce the acoustic wave back into an electrical signal.

Figure 1B:
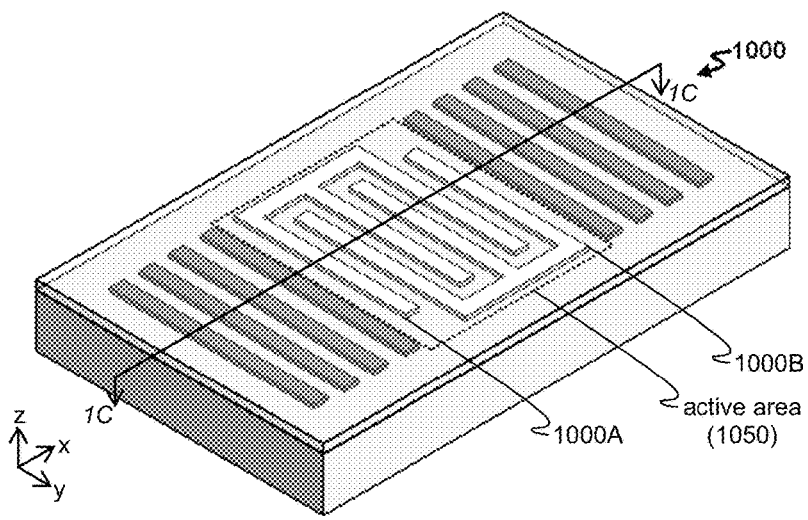

The electrode region can be characterized by a first edge and a second edge, in which the first and second edges are parallel to each other and are perpendicular to the propagation direction (i.e., the first direction). As seen in FIG. 1A, the electrode region includes a first electrode 130 and a second electrode 135. As seen in FIG. 1B, a first edge 1000A of the electrode region is defined to be along the y-axis and along an edge of the first finger in the first electrode 130; the second edge 1000B of the electrode region is also defined to be along the y-axis and along an edge of the last finger in the second electrode 135. When configured thusly, the propagation direction of the acoustic wave is along the x-axis.

Figure 2:
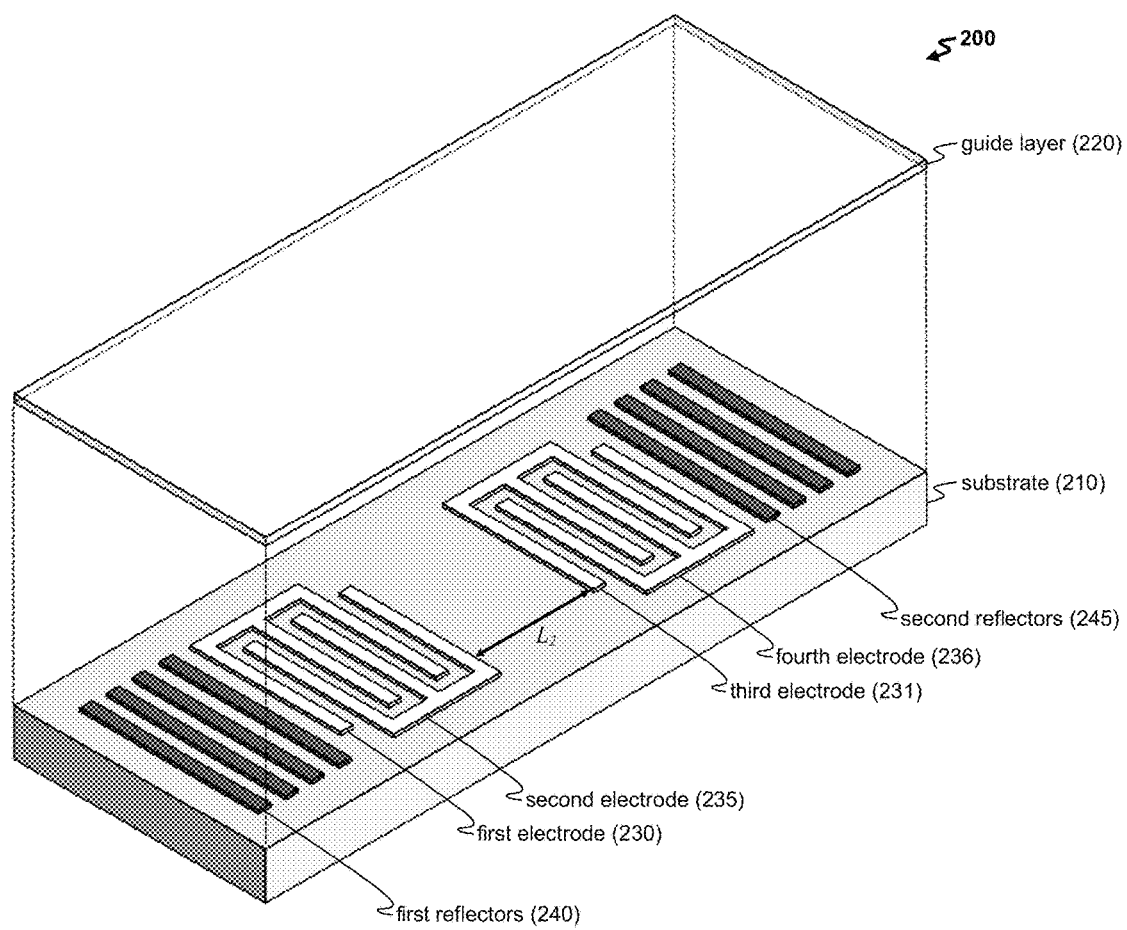
FIG. 2 shows a schematic of an exemplary two-port biosensor 200 having a spacing $L_2$ between two transducer pairs.

Turning again to FIG. 1A, the first electrode 130 and the second electrode 135 can be interdigitated transducers (IDT), in which comb electrodes are arranged to interdigitate the fingers of the electrodes. One of these electrodes can be an active electrode, and the other a grounded electrode. Each electrode can have any useful configuration and geometry. Other useful configurations and geometries for the electrodes can be employed. For instance, FIG. 2 provides a biosensor 200 having a two-port configuration, as described herein, in which two pairs of transducers are employed.

The biosensor can further include one or more reflector regions disposed on a surface of the piezoelectric substrate. The reflector region(s) are arranged to provide an acoustic cavity that confines the acoustic wave within a region of the piezoelectric substrate. As seen in FIG. 1A, the biosensor 100 can include a first reflector region having a plurality of first reflectors 140 and a second reflector region having a plurality of second reflectors 145. The reflector region can have any useful configuration and geometry (e.g., as described herein). The reflector region can include any type of reflector (e.g., a bar, a grating, an electrode, etc., in an optional array), which can be provided in a grounded configuration, an open configuration, and/or a closed configuration. For instance, a first reflector region can be located in proximity to a first edge 1000A of the electrode region; and the second reflector region can be located in proximity to a second edge 1000B of the electrode region. The distance between an edge of the first reflector region and the first edge of the electrode region can be any useful distance (e.g., as described herein).

In another instance, a major dimension of the reflector region can be configured to be parallel to the first edge of an electrode and perpendicular to the propagation direction (i.e., the first direction). As seen in FIG. 1B, the major dimension of the reflector region (e.g., a reflector length) is along the y-axis, and this major dimension is parallel to the first edge 1000A and perpendicular to the propagation direction that is along the x-axis.

The biosensor can include a guide layer in order to confine the surface acoustic wave to the surface, rather than allowing the wave to leak into the bulk substrate. FIG. 1A shows a guide layer 120 disposed above the substrate 110 and other components (e.g., including the first and second electrodes 130,135, as well as the first and second reflectors 140,145). To propagate a Love wave, the material and thickness of the guide layer can be optimized to provide a shear velocity that is lower than the shear velocity of the piezoelectric material. In another instance, the guide layer is selected to allow one or more capture agents to be bound to a surface of the guide layer (by way of indirect or direct binding). In an embodiment, the guide layer can be treated with one or more capture agents, thereby providing a functionalized surface. When that surface overlies the acoustic cavity, then a functionalized active area is formed. As seen in FIG. 1B, the assembled biosensor 1000 includes an active area 1050 located above the acoustic cavity bounded by the reflector regions, and this active area 1050 can be treated with one or more capture agents to form a functionalized active area.

Figure 1C:
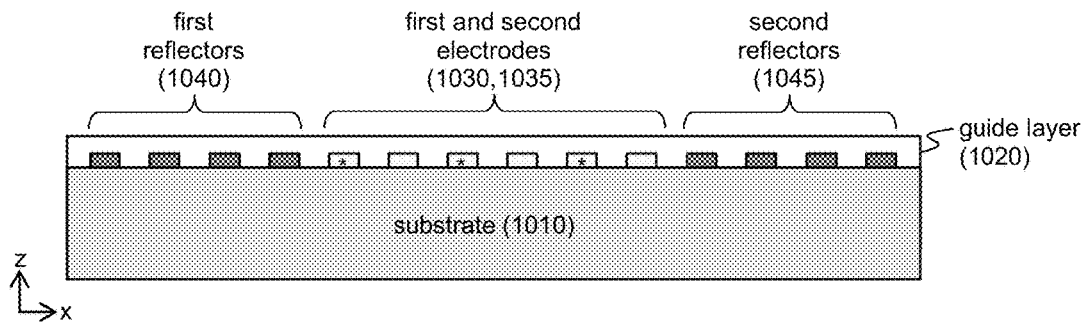

In yet another instance, the guide layer can be employed to electrically isolate the components of the biosensor, e.g., to isolate the fingers of the first electrode from the fingers of the second electrode. In this case, the material can be chosen to be a dielectric material (e.g., an insulator, such as a silicon oxide or a silicon nitride), which is disposed as a layer having a sufficient thickness that overlies the electrode region. FIG. 1C provides an exemplary biosensor in which the guide layer 1020 overlies a top surface of the substrate 1010, as well as the electrodes 1030,1035 of the electrode region and the first and second reflectors 1040,1045 of the reflector regions. In this configuration, the guide layer protects the components of the biosensor from the liquid sample.

The positions and configuration of the electrode regions and reflector regions can be optimized. In one instance, the reflector region(s) can be arranged in any useful location with respect to the electrode region. For example, the electrode region can include one or more transducers, which in turn are arranged to provide an acoustic wave that propagates along a first direction. To effectively isolate and confine that wave, the reflection region can be arranged to interfere and reflect the acoustic wave a multiple of times within an active area. In one instance, the reflector region has a first reflective edge, and this edge is positioned to be perpendicular to the first direction (i.e., the propagation direction of the acoustic wave). Furthermore, to minimize destructive interference and maximize reflection, the reflector region can be positioned to be in proximity to an edge of the electrode region (e.g., separated by a distance d that is a fractional portion of the characteristics acoustic wavelength $\lambda$, such as $\pm 1/8\lambda$, $\pm 1/4\lambda$, $\pm 3/8\lambda$, $\pm 1/2\lambda$, $\pm 3/4\lambda$, etc.).

Figure 1D:
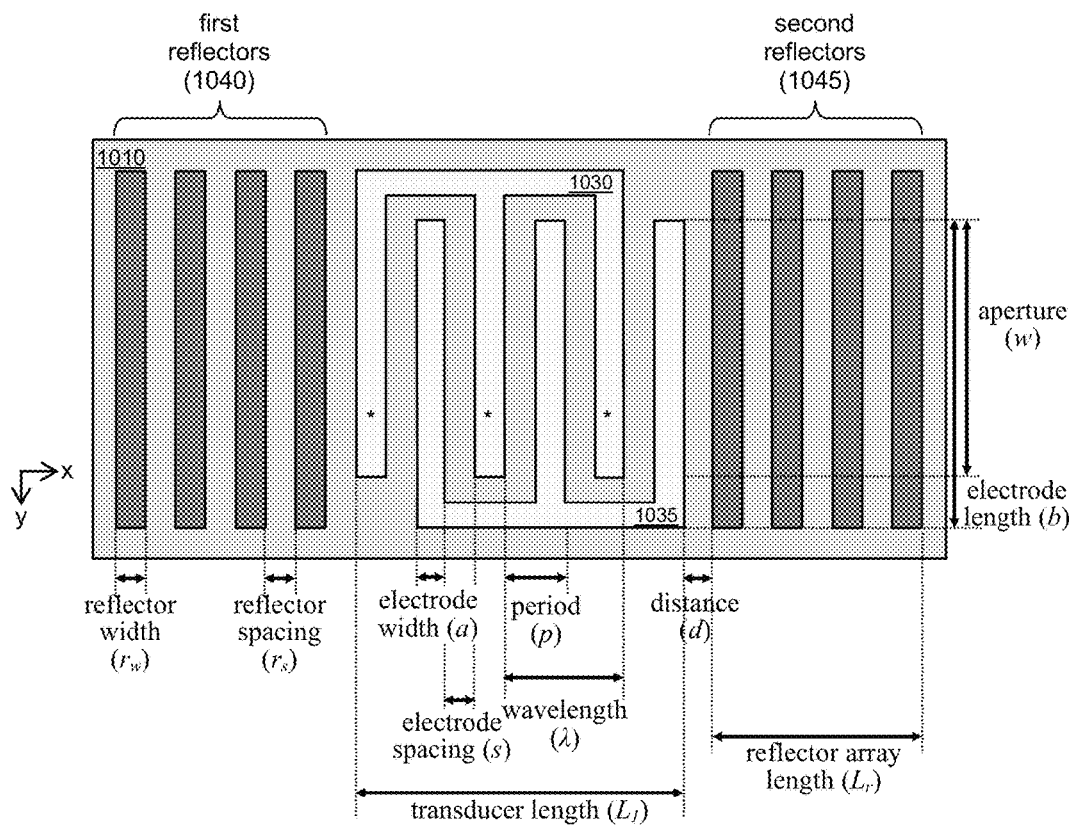

FIG. 1D provides dimensions of the electrode regions and reflector regions that can be optimized. For instance, the electrode region (including the first and second electrodes 1030,1035) and the reflector regions (including the first and second reflectors 1040,1045) can be arranged on the substrate 1010 in any useful manner.

The dimensions of the electrode region include a length of the electrode region or transducer length $L_1$ (e.g., of from about $10\lambda$ to about $500\lambda$, such as of from $50\lambda$ to $500\lambda$ or $100\lambda$ to $500\lambda$); a spacing $L_2$ between two electrode regions (e.g., as in FIG. 2, in which $L_2$ can be of from about $10\lambda$ to about $500\lambda$, such as of from $50\lambda$ to $500\lambda$ or $100\lambda$ to $500$); and an aperture w along a length of an electrode region or a dimension that is perpendicular to the propagation direction (e.g., an aperture w along the y-axis, in which w is of from about $20\lambda$ to about $500\lambda$ e.g., such as from $20\lambda$ to $100\lambda$, and/or of from about 10 μm to about 500 μm (e.g., such as from 50 μm to 500 μm or from 100 μm to 500 μm). Other dimensions include those for individual electrodes or electrode fingers, such as an electrode width a along the propagation direction (e.g., along the x-axis, in which a is a width of $\lambda/8$, $\lambda/4$, $3\lambda/8$, or $\lambda/2$. In various embodiments, a has a width ranging from about 1 μm to about 4 μm); an electrode spacing s along the propagation direction (e.g., along the x-axis) and between the individual electrodes or individual electrode fingers (e.g., such as s=a, n×a, or a/n, in which n=1, 2, 3, . . . m); a period p along the propagation direction (e.g., along the x-axis, in which p=a+s; or in which p is of from about 2 μm to about 100 μm); an acoustic wavelength $\lambda$ (e.g., in which $\lambda=2p$ or, when a=s, then $\lambda=4a$);

an electrode length b (e.g., along the y-axis, such as of from about 50 μm to about 1000 μm; and/or of from about 20λ to about 500λ); a thickness $t_e$ of the electrode (e.g., along the z-axis, where the normalized thickness of the electrode is determined as $t_e/\lambda$, which can be of from about 1% to about 6%, such as from 3% to 6%); and an $n_e$ number of individual electrodes or $n_e$ number of pairs of electrodes, such as in an interdigitated transducer, in which $n_e$ is any number of from about 0.5 to about 500.

The electrode region can be configured to provide the operating frequency of the transducer, in which operating frequency $f_O=v_s/\lambda$, where $v_s$ is the shear velocity of the SH wave (e.g., of from about 3000 m·s$^{-1}$ to 6000 m·s$^{-1}$, such as about 4000 m·s$^{-1}$) and λ is the acoustic wavelength. The acoustic wavelength λ, in turn, can be determined lithographically. For instance, λ is generally twice the characteristic period of the electrode or electrode array (e.g., λ=2p), and this period p can be lithographically defined by patterned interdigitated electrodes having a particular electrode width a and electrode spacing s (e.g., p=a+s). The shear velocity $v_s$ is determined by the underlying substrate, as well as any overlying layers (e.g., guide layers).

The biosensor can be configured to operate at any useful frequency $f_O$. Useful frequencies can include frequencies from about 80 MHz to about 3 GHz, such as of from 80 MHz to 200 MHz, 80 MHz to 300 MHz, 80 MHz to 375 MHz, 80 MHz to 450 MHz, 80 MHz to 600 MHz, 80 MHz to 750 MHz, 80 MHz to 1 GHz, 80 MHz to 2 GHz, 80 MHz to 2.5 GHz, 100 MHz to 200 MHz, 100 MHz to 300 MHz, 100 MHz to 375 MHz, 100 MHz to 450 MHz, 100 MHz to 600 MHz, 100 MHz to 750 MHz, 100 MHz to 1 GHz, 100 MHz to 2 GHz, 100 MHz to 2.5 GHz, 100 MHz to 3 GHz, 200 MHz to 300 MHz, 200 MHz to 375 MHz, 200 MHz to 450 MHz, 200 MHz to 600 MHz, 200 MHz to 750 MHz, 200 MHz to 1 GHz, 200 MHz to 2 GHz, 200 MHz to 2.5 GHz, 200 MHz to 3 GHz, 350 MHz to 450 MHz, 350 MHz to 600 MHz, 350 MHz to 750 MHz, 350 MHz to 1 GHz, 350 MHz to 2 GHz, 350 MHz to 2.5 GHz, 350 MHz to 3 GHz, 400 MHz to 450 MHz, 400 MHz to 600 MHz, 400 MHz to 750 MHz, 400 MHz to 1 GHz, 400 MHz to 2 GHz, 400 MHz to 2.5 GHz, 400 MHz to 3 GHz, 425 MHz to 450 MHz, 425 MHz to 600 MHz, 425 MHz to 750 MHz, 425 MHz to 1 GHz, 425 MHz to 2 GHz, 425 MHz to 2.5 GHz, 425 MHz to 3 GHz, 450 MHz to 600 MHz, 450 MHz to 750 MHz, 450 MHz to 1 GHz, 450 MHz to 2 GHz, 450 MHz to 2.5 GHz, 450 MHz to 3 GHz, 475 MHz to 600 MHz, 475 MHz to 750 MHz, 475 MHz to 1 GHz, 475 MHz to 2 GHz, 475 MHz to 2.5 GHz, 475 MHz to 3 GHz, 500 MHz to 600 MHz, 500 MHz to 750 MHz, 500 MHz to 1 GHz, 500 MHz to 2 GHz, 500 MHz to 2.5 GHz, 500 MHz to 3 GHz, 550 MHz to 600 MHz, 550 MHz to 750 MHz, 550 MHz to 1 GHz, 550 MHz to 2 GHz, 550 MHz to 2.5 GHz, 550 MHz to 3 GHz, 600 MHz to 750 MHz, 600 MHz to 1 GHz, 600 MHz to 2 GHz, 600 MHz to 2.5 GHz, or 600 MHz to 3 GHz. In alternative embodiments, the frequency $f_O$ is limited by lithographic limits (e.g., up to about 2.5 GHz, in one or more embodiments).

The electrode region(s) and reflector region(s) can be configured to optimize acoustic cavity performance. These regions can be designed for optimum coupling between the spatial periodic electrical field that accompanies the acoustic standing wave. For instance, the electrode region can be optimized by centering each electrode at the peaks of the electromagnetic field, and the reflector region can be optimized by ensuring that the Bragg frequency of the reflectors is substantially similar to the transducer frequency. Reflectors can be characterized by a Bragg frequency $f_B$, at which $\lambda_B=2p$, where p is the period for the reflectors (e.g., p=$r_s$ or p=$r_s$+$r_w$). In yet another instance, resonant conditions can be attained when the ratio of the spacing $L_2$ between two transducer pairs and the Bragg wavelength $\lambda_B$ is a fractional integer (e.g., $L_2/\lambda_B$=n/2+¼, in which n=1, 2, 3, . . . m).

The dimensions of the reflector region include a length of the reflector region or reflector array length $L_r$ (e.g., of from about 100 μm to about 1000 μm); a reflector width $r_w$ along the propagation direction (e.g., along the x-axis); a reflector spacing $r_s$ along the propagation direction (e.g., along the x-axis) and between the individual reflectors; a reflector length $r_l$ (e.g., along the y-axis, such as of from about 50 μm to about 500 μm; and/or of from about 20λ to about 50λ); a thickness $t_r$ of the reflector (e.g., along the z-axis, in which in some non-limiting embodiments, $t_r$=$t_e$); a center-to-center distance between two reflector regions (e.g., of from about 150λ to about 300λ); and an $n_r$ number of individual reflectors or $n_r$ number of pairs of reflectors, such as in an interdigitated reflector, in which $n_r$ is any number of from about 0.5 to about 500. In addition, the distance d between the electrode region and the reflector region can be any useful distance, e.g., a multiple of the acoustic wavelength λ, λ/8, λ/4, or λ/2, such as nλ/2, nλ/8, (2n+1)λ/8, (2n−1)λ/4, (4n+1)λ/8, or (4n+3)λ/8, in which n=1, 2, 3, . . . m; or in which the distance is of from about 0.1λ to about 3λ.

FIG. 2 shows a biosensor 200 having a two-port configuration, in which the electrode region and reflector regions are disposed on a substrate 210 and under a guide layer 220. The biosensor 200 includes an electrode region, which in turn includes a first pair of transducer (having first and second electrodes 230,235) and a second pair of transducers (having third and fourth electrodes 231,236). The electrode region also includes a spacing $L_2$ located between the first and second pairs of transducers. This spacing $L_2$ can be of any useful dimension that is, e.g., sufficient to efficiently propagate an acoustic wave with minimal loss, to maintain an acoustic cavity, to accommodate a fluid sample, to bind to a sufficient surface concentration of capture agents, and/or to capture a sufficient mass of a desired target. For this two-port configuration, the first and second reflectors 240,245 can be of any useful distance d between the electrode region and each of the first and second reflector regions.

Piezoelectric Substrate and Guide Layers

The piezoelectric substrate can include any useful piezoelectric material. Exemplary piezoelectric materials include lithium tantalate (LiTaO$_3$), lithium niobate (LiNbO$_3$), potassium niobate (KNbO$_3$), quartz (SiO$_2$, such as an α-SiO$_2$), langatate (La$_3$Ga$_{5.5}$Ta$_{0.5}$O$_{14}$), langasite (La$_3$Ga$_5$SiO$_{14}$), langanite (La$_3$Ga$_{5.5}$Nb$_{0.5}$O$_{14}$), lead zirconate titanate (Pb[Zr$_x$Ti$_{1-x}$]O$_3$, where 0≤x≤1, such as PbZr$_{0.52}$Ti$_{0.48}$O$_3$), cadmium sulfide (CdS), berlinite (AlPO$_4$), gallium phosphate (GaPO$_4$), lithium iodate (LiIO$_3$), lithium tetraborate (Li$_2$B$_4$O$_7$), bismuth germanium oxide (Bi$_{12}$GeO$_{20}$), zinc oxide (ZnO), aluminum nitride (AlN), etc., provided in any useful orientation, e.g., 36° YX LiTaO$_3$, Y+36° cut LiTaO$_3$, 0° X-cut LiTaO$_3$, 128° XY LiNbO$_3$, 41° YX LiNbO$_3$, 64° YX LiNbO$_3$, rotated Y-cut quartz, or 36° Y quartz.

In some embodiments, the piezoelectric substrate is obtained from a particular crystal cut that propagates and supports SH waves or leaky SH waves. In other embodiments, the electrode region is arranged on that particular crystal cut of the piezoelectric substrate to effectively launch the SH wave. In other embodiments, the piezoelectric substrate includes a piezoelectric crystal layer that is approximately thicker than the Love wave penetration depth, in which the crystal layer is optionally disposed on a non-piezoelectric substrate. Such piezoelectric substrate can include one or more electrode regions (e.g., any described herein), in which the components of the electrode regions are arranged to provide a useful acoustic propagation path along any directional axis that provides a useful acoustic wave (e.g., an SH acoustic wave).

The guide layer can overlie a top surface of the piezoelectric substrate, or a portion of this top surface. Such a guide layer can be used to propagate a Love wave confined to the guide layer. In addition, a functionalized active area can include one or more capture agents disposed on the guide layer. The guide layer can be formed of any useful material, such as a polymer (e.g., a polystyrene, a polyimide, a polynorbornene, a perfluoropolymer, a poly(xylylene) (e.g., parylene C or poly(chloro-p-xylylene)), poly(dimethylsiloxane), or a polymethylmethacrylate (PMMA)), an oxide (e.g., ZnO), or a dielectric (e.g., a silicon oxide, such as $SiO_2$; a silicon oxynitride, e.g., SiON; or a silicon nitride, such as $Si_3N_4$, which can optionally including one or more dopants). The guide layer can be of any useful thickness, such as of from about 0.05 µm to about 20 µm (e.g., from 0.05 µm to 1 µm, 0.05 µm to 2 µm, 0.05 µm to 5 µm, 0.05 µm to 10 µm, 0.1 µm to 1 µm, 0.1 µm to 2 µm, 0.1 µm to 5 µm, 0.1 µm to 10 µm, 0.1 µm to 20 µm, 0.5 µm to 1 µm, 0.5 µm to 2 µm, 0.5 µm to 5 µm, 0.5 µm to 10 µm, 0.5 µm to 20 µm, 1 µm to 2 µm, 1 µm to 5 µm, 1 µm to 10 µm, 1 µm to 20 µm, 2 µm to 5 µm, 2 µm to 10 µm, 2 µm to 20 µm, 5 µm to 10 µm, or 5 µm to 20 µm).

Any method known in the art for depositing a guide layer may be used, e.g., such as plasma enhanced chemical vapor deposition. On top of the guide layer, a thin layer of a non-reactive liquid silicone material (e.g., a hexamethyldisilazane, oligodialkylsiloxane, polydialkylsiloxane, or other silicone, such any silanizing compound described herein) or any other non-reactive liquid may be used to prepare the surface for further functionalization. The guide layer, or a portion thereof, can include one or more linkers, binding agents, and/or capture agents (e.g., any described herein).

Electrode Region

The electrode region can include any number of electrical components configured to deliver an electrical signal to the piezoelectric substrate, in which that electrical signal is transduced to provide an acoustic wave. The electrode region can include one or more electrodes configured in any useful manner. The electrodes can form a delay line, which can be optionally shorted. In addition, such lines can be unidirectional or bidirectional. The electrodes can be of any useful configuration (e.g., an interdigitated configuration, an arrayed configuration, a gate configuration, a one-port configuration, a two-port configuration, a delay line configuration, a unidirectional configuration, a bidirectional configuration, etc.), geometry (e.g., bar electrodes, single finger electrodes, double finger electrodes, split finger electrodes, pruned double split finger electrodes, etc.), orientation (e.g., having a major axis that is orthogonal to a first direction that is the propagate direction of the acoustic wave and/or configured to provide an acoustic wave along a crystal cut or axis that supports SH waves), or electrical connection (e.g., shorted, grounded, open, closed, arrayed, etc.).

Each port can include any useful electrode configuration. In one instance, each port can include a first electrode (e.g., an active electrode) and a second electrode (e.g., a ground electrode). In a one-port configuration, the first port includes a first electrode and a second electrode, in which the first electrode is active and the second electrode is grounded. An applied voltage results in an acoustic wave that is transmitted from the first electrode and received by the second electrode. In a two-port configuration, a first port includes a first electrode and a second electrode, and a second port includes a third electrode and a fourth electrode. A spacing $L_2$ is present between the first and second ports. In use, an applied voltage between the electrodes of the first port results in an acoustic wave, which propagates through the spacing $L_2$ of the piezoelectric substrate. This wave is then received by the second port. In some instances, the first and second ports are different. In other instances, the first and second ports are identical.

Electrodes can have any useful configuration. In one instance, the electrodes form an interdigitated transducer (IDT), in which the fingers of each electrode are interdigitated. The design of the IDT can be selected from single finger electrodes, double split finger electrodes, pruned double split finger electrodes, or unidirectional electrodes. For instance, FIG. 1D shows an IDT including single finger electrodes 1030,1035, in which these electrodes are interdigitated. The electrodes have a single finger configuration, as seen by the presence of one electrode finger in each period p.

In another instance, the IDT includes a pair of opposing comb-shaped electrodes (a first electrode and a second electrode), each electrode having a fingerlike periodic pattern of electrode fingers interdigitated with the electrode fingers of the opposing comb-shaped electrode. An acoustic cell within the IDT is defined in terms of the periodicity p of the finger structure that is specified in terms of the acoustic wavelength λ. This cell pattern often repeats for a specific number of wavelengths which defines the overall acoustic length of the IDT. When a RF drive voltage is applied to the comb-shaped electrodes of the transmitting IDT, a spatially periodic, surface-concentrated electric field distribution is established between the spatially periodic electrode fingers that penetrate into the piezoelectric substrate. Because of the piezoelectric coupling, an elastic strain distribution with periodicity is created in the substrate, thereby generating the acoustic wave. To generate the correct acoustic wave, the proper axis of the piezoelectric crystal is preferably aligned with the IDT. The strength of the outputted acoustic wave can be controlled by changing the overlap of the electrodes as determined by an aperture w, a number $n_e$ of finger pairs, their periodic p, the finger pattern, and the power input.

Figure 5A:
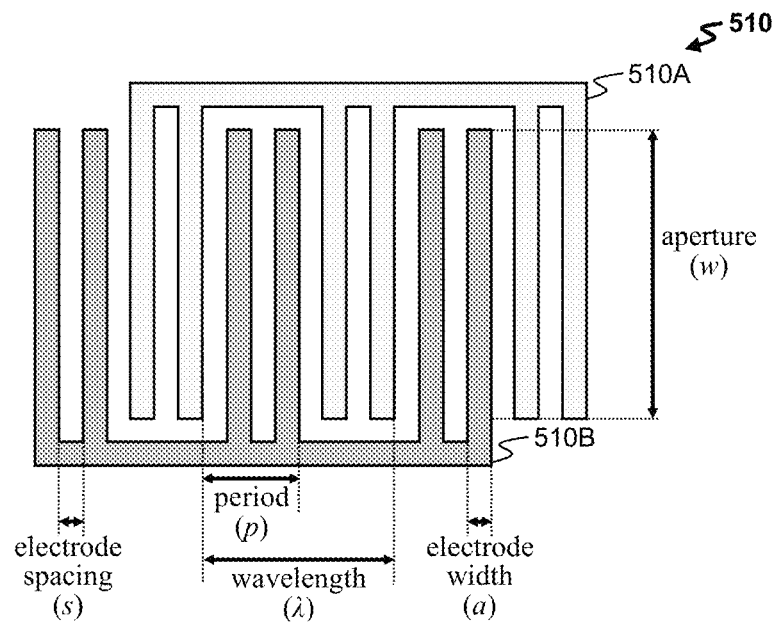
FIG. 5A-5D shows exemplary electrode regions including (A) a pair 510 of dual finger transducers, (B) a pair 520 of split finger transducers, (C) another pair 530 of split finger transducers, and (D) a pair 540 of single finger and dual finger transducers.

In yet another instance, FIG. 5A shows a pair of double split finger electrodes, which includes a first comb-shaped electrode having double split fingers 510A and a second comb-shaped electrode having double split fingers 510B. Two electrode fingers are present in each period p, and two fingers from each electrode 510A,510B are present in each wavelength λ. Each electrode (e.g., any electrode herein, including electrodes 510A,510B) can have the same or different width a, as well as the same or different spacing s. Based on the overlap of the electrodes, any useful aperture w can be designed. In some instances, one electrode from a port (e.g., a pair of electrodes) can be grounded to provide an electrical path. In yet another instance, the double split finger electrodes can be modified as a pruned configuration, in which every other finger pairs are removed from the double split finger design, thereby increasing the spacing between a finger pair of a first electrode from a finger pair of a second electrode. This design can maintain the lower insertion loss of a double split finger transducer with the equivalent number of finger pairs but has a narrower pass band. The pruned design can also reduce the internal reflections that would occur in a double split finger design having the full amount of finger pairs.

In another aspect, the double split finger electrodes can be modified using a weighting technique, in which a single finger is followed by a split finger to create the finger pair. Such a design can provide a unidirectional acoustic wave, which directs the acoustic energy. This design is also referred to as a single-phase unidirectional transducer (SPUDT) and has the advantage of low interfering reflections and low insertion loss.

A SPUDT deliberately includes reflections (by way of including reflector electrodes) internal to the transducer to cancel the effects of regeneration reflection. The SPUDT can be a double-metallization SPUDT structure, a natural SPUDT (NSPUDT), or an electrode-width-controlled SPUDT (EWC-SPUDT) (e.g., in which a cell for the EWC-SPUDT includes a $\lambda/8$ excitation electrode finger and $\lambda/8$ and $\lambda/4$ reflection electrode fingers, where the finger spacings s are optimized to excite or detect shear-horizontal waves that are in-phase along the length of each transducer in the presence of the guiding layer and the sensing region). Other electrode configurations are described in U.S. Pat. Nos. 5,073,763, 6,777,855, 7,173,360, 7,878,063, 8,436,509, and 8,669,688, each of which is incorporated herein by reference in its entirety.

Figure 5B:
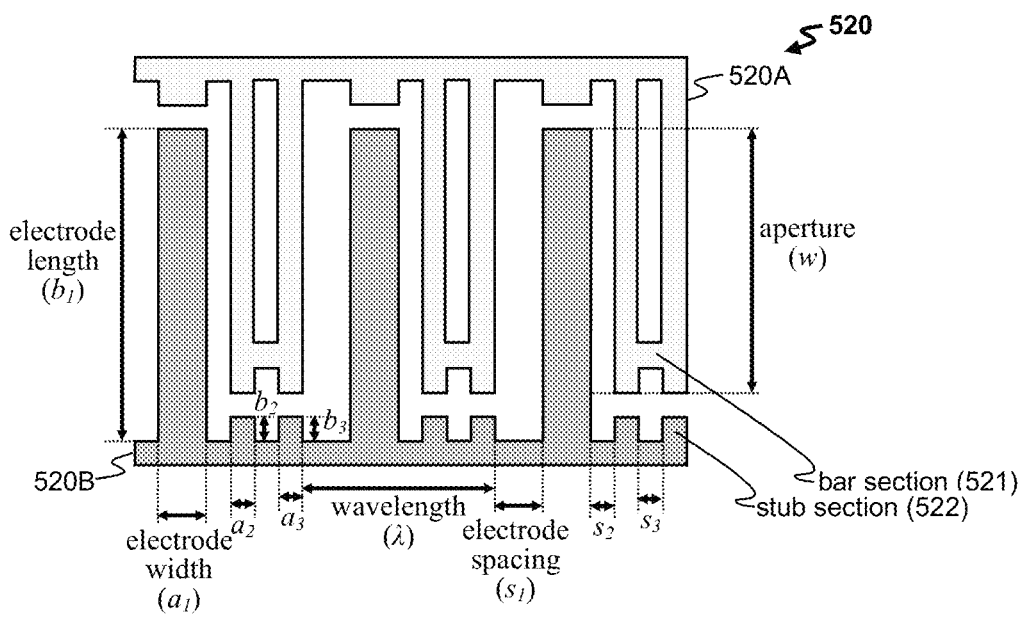

The EWC-SPUDT can have any useful configuration. FIG. 5B shows an exemplary EWC-SPUDT configuration 520 having a first comb-shaped electrode having split fingers 520A and a second comb-shaped electrode having single fingers 520B. In one instance, each SPUDT cell has a length of $\lambda$. In addition, each cell includes a distributed reflector having a single excitation electrode finger with an electrode length $b_1$ and width $a_1$ (e.g., $a_1=\lambda/8$). This single finger extends from electrode 520B, which also has a plurality of stub sections 522 with lengths $b_2,b_3$. The cell also includes split finger reflection electrodes extending from electrode 520A, in which a bar section 521 connects the reflection electrodes (e.g., a split finger electrode having a first finger of width $a_2$ of $\lambda/8$ and a second finger of width $a_3$ of $\lambda/4$).

Figure 5C:
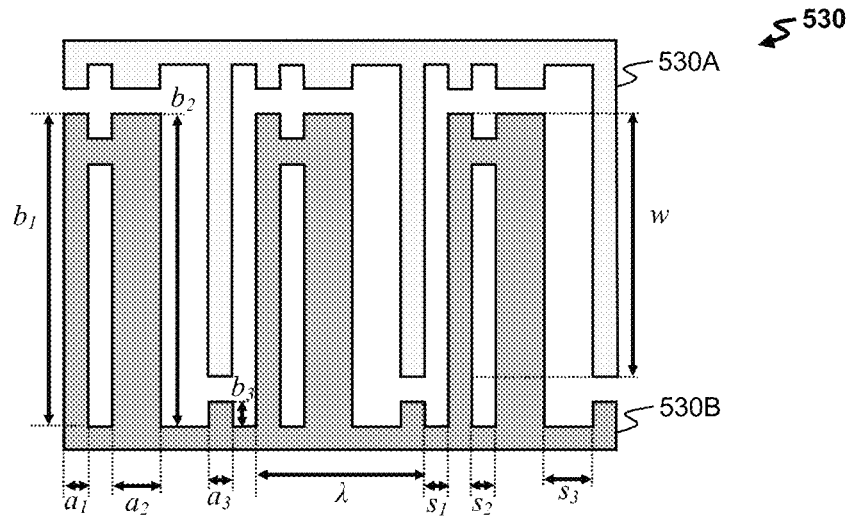

Each electrode can have any useful width $a_1$, $a_2$, $a_3$, as well as any useful spacing $s_1$, $s_2$, $s_3$. For instance, FIG. 5C provides another embodiment of a SPUDT design in which various dimensions (e.g., one or more of width $a_1$, $a_2$, $a_3$, length $b_1$, $b_2$, $b_3$, and/or spacing $s_1$, $s_2$, $s_3$ dimensions) are varied. This configuration 530 provides a first comb-shaped electrode 530A having single fingers and a second comb-shaped electrode 530B having split finger reflection electrodes connected by a bar section.

Figure 5D:
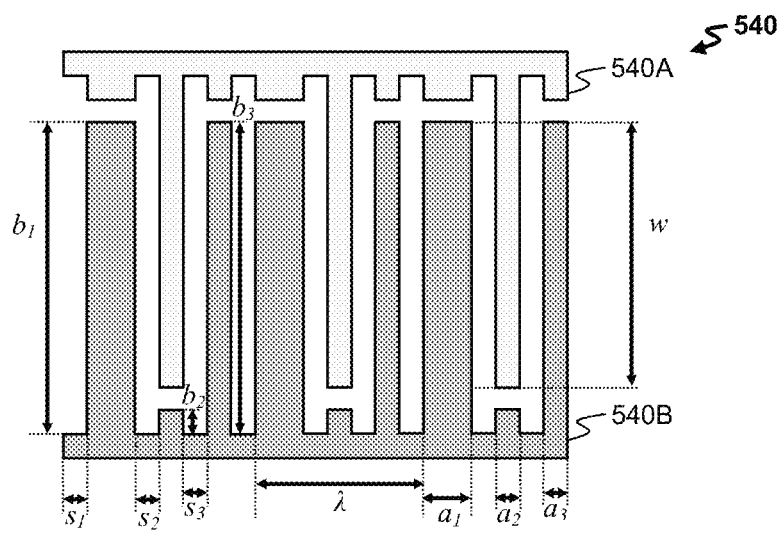

In another instance, FIG. 5D provides another embodiment of a SPUDT design lacking bar sections. This configuration 540 provides a first comb-shaped electrode 540A having single fingers and a second comb-shaped electrode 540B having double fingers lacking a bar section. Additional SPUDT cells can be used to produce a smaller passband; and other SPUDT designs and optimization procedures are described in Shui Y et al., "Optimization of single-phase, unidirectional transducers using three fingers per period," *IEEE Trans. Ultrason. Ferroelectr. Freq. Control* 2002; 49(12): 1617-21, which is incorporated herein by reference in its entirety.

The transducer length $L_1$ for each port (or electrode pair) can be of any useful dimension. In one instance, $L_1$ is determined based on a multiple of the characteristic acoustic wavelength $\lambda$. Exemplary $L_1$ includes of from about $10\lambda$ to about $500\lambda$ (e.g., about $197\lambda$, or from $50\lambda$ to $500\lambda$). Each transducer can include any useful number $n_e$ of fingers or finger pairs, such as of from about 10 to 500 fingers or finger pairs (e.g., from 50 to 500 fingers or finger pairs). The period p can be of any useful dimension, such as of from about 2 µm to about 100 µm (e.g., of from 2 µm to 90 µm, 2 µm to 75 µm, 2 µm to 50 µm, 2 µm to 40 µm, 2 µm to 25 µm, 2 µm to 10 µm, 5 µm to 100 µm, 5 µm to 90 µm, 5 µm to 75 µm, 5 µm to 50 µm, 5 µm to 40 µm, 5 µm to 25 µm, 5 µm to 10 µm, 8 µm to 100 µm, 8 µm to 90 µm, 8 µm to 75 µm, 8 µm to 50 µm, 8 µm to 40 µm, 8 µm to 25 µm, 8 µm to 10 µm, 10 µm to 100 µm, 10 µm to 90 µm, 10 µm to 75 µm, 10 µm to 50 µm, 10 µm to 40 µm, 10 µm to 25 µm, 15 µm to 100 µm, 15 µm to 90 µm, 15 µm to 75 µm, 15 µm to 50 µm, 15 µm to 40 µm, 15 µm to 25 µm, 20 µm to 100 µm, 20 µm to 90 µm, 20 µm to 75 µm, 20 µm to 50 µm, 20 µm to 40 µm, 20 µm to 25 µm, 25 µm to 100 µm, 25 µm to 90 µm, 25 µm to 75 µm, 25 µm to 50 µm, 25 µm to 40 µm, 30 µm to 100 µm, 30 µm to 90 µm, 30 µm to 75 µm, 30 µm to 50 µm, or 30 µm to 40 µm, such as about 10 µm). For each transducer, the metallization ratio $\eta$ can be determined as a ratio of the electrode width a to the period p, and this ratio can be any useful value (e.g., $\eta=a/p$ of from about 0.4 to about 0.75).

The aperture w for each port (or electrode pair) can be of any useful dimension. In one instance, aperture w is determined based on a multiple of the characteristic acoustic wavelength $\lambda$. Exemplary w includes of from about $20\lambda$ to about $200\lambda$ (e.g., about $47\lambda$); or from about 10 µm to about 500 µm (e.g., about 200 µm).

The electrodes can be formed of any suitable conductive material. Exemplary materials include aluminum, gold, chromium, silver, with an optional adhesion layer (e.g., including titanium), as well as alloys thereof. In addition, each electrode can include one or more lines (e.g., bonding wires), which in turn may optionally be connected to one or more contacts (e.g., contact pads configured to provide an electrical connection to the electronics module).

Reflector Regions

The biosensor can include one or more reflector regions configured to support an acoustic cavity. Such reflector regions can include one or more electrodes (e.g., any configuration or design described herein) that are grounded and/or shorted. In some embodiments, the reflector region includes an array of reflectors, where any number of reflectors $n_r$ may be present in the array (e.g., of from about 10 to about 500). Furthermore, each reflector can have any useful dimension (e.g., any useful reflector length $r_l$ or reflector width $r_w$), configuration (e.g., any useful reflector spacing $r_s$ or number of reflectors $n_r$), or design (e.g., a bar electrode, a strip electrode, a grating design, etc.).

Figure 6A:
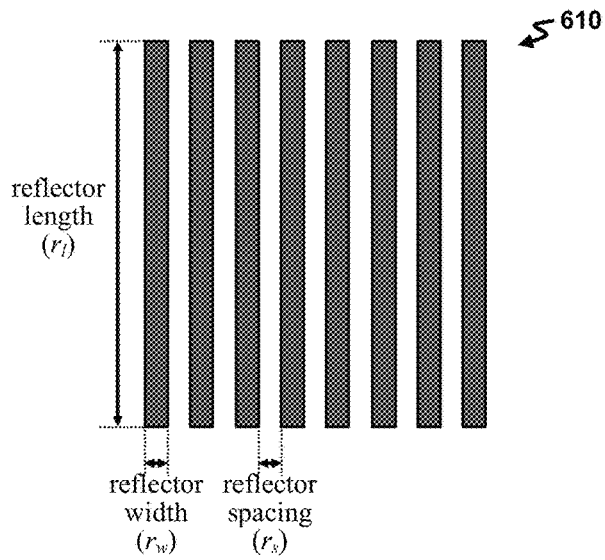
FIG. 6A-6E shows exemplary reflector regions including (A) an array 610 of bar reflectors, (B) a grating reflector 620, (C) a pair 630 of reflectors, (D) a pair 640 of split finger reflectors, and (E) a pair 650 of split finger and elongated finger reflectors.

FIG. 6A provides an exemplary reflector region 610 having an array of bar reflectors. Each reflector can have any useful reflector length $r_l$ (e.g., such as of from about 50 µm to about 500 µm), reflector width $r_w$ (e.g., such as a multiple of the acoustic wavelength $\lambda$, $\lambda/8$, $\lambda/4$, or $\lambda/2$, such as $n\lambda/2$, $n\lambda/8$, $(2n+1)\lambda/8$, $(2n-1)\lambda/4$, $(4n+1)\lambda/8$, or $(4n+3)\lambda/8$, in which n=1, 2, 3, . . . m; and/or of from about 10 nm to about 250 µm, such as of from 1 µm to 100 µm), or reflector spacing $r_s$ (e.g., such as $r_s=r_w$, $n\times r_w$, or $r_w/n$, in which n=1, 2, 3, . . . m).

Figure 6B:
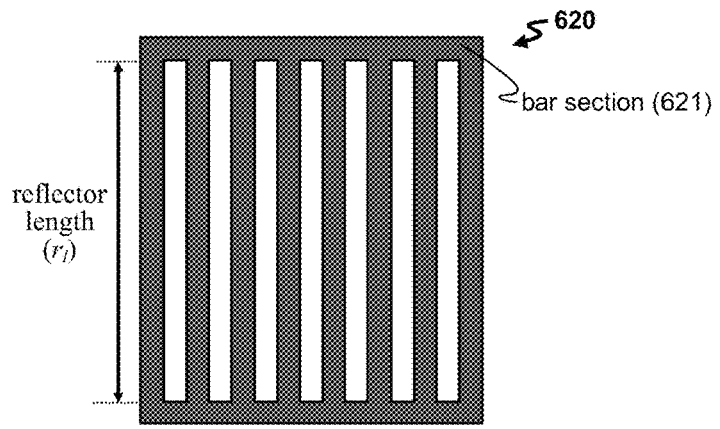
Figure 6C:
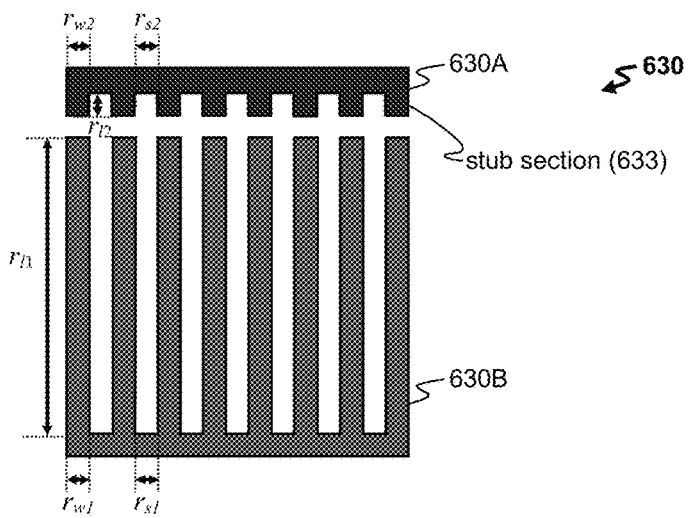

The reflector region can include reflectors having any useful design. FIG. 6B shows a reflector region 620 having a grating design, in which the individual reflectors are connected by a bar section 621 to form a grating. Alternatively, each reflector region can include two or more reflectors. FIG. 6C shows a region 630 with a first reflector 630A and a second reflector 630B. The first reflector 630A includes stub sections 633 projecting from a bar section, and each stub is characterized by a particular width $r_{w2}$, length $r_{l2}$, and spacing $r_{s2}$ between the stubs. The second reflector 630B includes fingers, and each finger is characterized by a particular width $r_{w1}$, length $r_{l1}$, and spacing $r_{s1}$ between the fingers. The first and second reflectors can be aligned (e.g., to provide a stub section that is aligned with each finger section, e.g., along the y-axis).

Figure 6D:
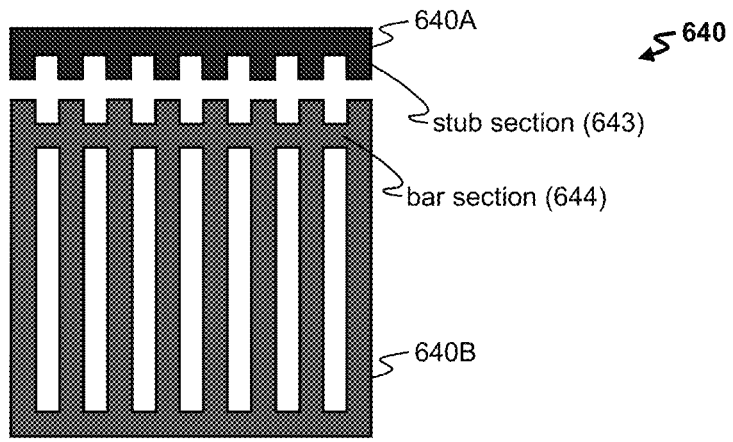
Figure 6E:
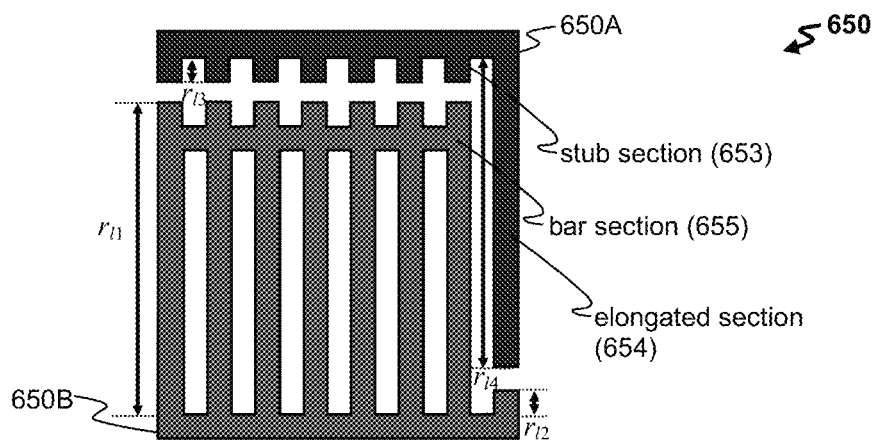

Reflectors can have any useful feature to effectively reflect transmitted acoustic waves. In one instance, as seen in FIG. 6D, the reflector region 640 includes a first reflector 640A having stub sections 643 and a second reflector 640B having a bar section 644 that connects each finger. In yet another instance, as seen in FIG. 6E, the reflection region 650 includes a first reflector 650A having stub sections 653 (having a length $r_{f3}$) and an elongated section 654 (having a length $r_{f4}$) at the end of the cell. The region also includes a second reflector 650B having a bar section 655 that connects each finger (having a length $r_{f1}$) and a shortened finger (having a length $r_{f2}$).

The reflectors can be formed of any useful material, including, but not limited to, aluminum, gold, chromium, silver, platinum, with an optional adhesion layer (e.g., including titanium), as well as alloys thereof. In one non-limiting example, the reflectors are composed of the same material as the electrodes, e.g., to simplify fabrication of the biosensor.

Functionalized Active Area

The functionalized area can include any useful combination of capture agents (e.g., any described herein) configured to bind one or more targets. In addition, the functionalized active area is located in a region of the biosensor to facilitate sensitive detection of any mass changes occurring in this area. In one instance, the functionalized active area is disposed in proximity to (e.g., above) the acoustic cavity. Furthermore, the functionalized active area can include a portion of the guide layer within the acoustic cavity.

The functionalized active area can have any useful dimension. For instance, in a one-port configuration, one dimension of the active area is determined by the transducer length $L_1$. In another instance, in a two-port configuration, one dimension of the active area is determined by the spacing $L_2$ between two transducer pairs. Each of $L_1$ and $L_2$ can have any useful dimension, such as of from about 50λ to about 500λ (e.g., of from 50λ to 200λ) and/or of from about 50 μm to about 800 μm. In another instance, a second dimension of the active area is determined by the electrode length b (e.g., any described herein, such as of from about 50 μm to about 500 μm). In yet another instance, $L_1$ and $L_2$ is less than the length of the reflector region $L_r$ to suppress ripples (e.g., a ratio $L_r/L_1$ or $L_r/L_2$ of from about 2 to about 10). Other exemplary reflector region designs are described in U.S. Pat. Nos. 4,837,476, 6,848,295, 7,500,379, 7,679,474, and 9,048,807, as well as U.S. Pub. No. 2009/0282902, each of which is incorporated herein by reference in its entirety.

In addition, to ensure selective detection of the desired target, the functionalized active area can include one or more capture agents configured to bind one or more targets. Any useful capture agent can be employed, e.g., antibodies, proteins, etc., such as any described herein. Further, the capture agent can be directly or indirectly attached to a surface using covalent bonds and/or non-covalent bonds (e.g., via van der Waals forces, hydrogen bonds, and/or other intermolecular forces). For direct attachment, the capture agent can be adsorbed to the surface or reacted with a functional group present on the surface. For indirect attachment, the capture agent can be attached to a linker (e.g., any described herein), and this linker can in turn be directly or indirectly attached to the surface.

The surface can be a portion of the guide layer within the acoustic cavity. This surface can be treated in any useful manner to allow for direct or indirect attachment of a capture agent. The surface can be treated to provide a reactive group or a reactive layer. For instance, if the surface includes siloxane (Si—O—Si) bonds, then the surface can be oxidized to provide reactive silanol (Si—O—H) bonds.

In another instance, the surface can be treated with one or more binding agents that in turn provide a reactive group or a reactive layer (e.g., a reactive layer including an epoxide group, an amino group, a hydroxyl group, an alkoxy group, etc.). If the surface is treated to include a reactive layer having an epoxide group, then one or more capture agents having a nucleophile (e.g., an amino group) can be employed in a ring-opening reaction with the epoxide, thereby covalently attaching that capture agent to the surface by way of the reactive layer. One or more reactive layers can be employed on the surface to attach one or more linkers (e.g., between the surface and the capture agent, between the binding agent and the capture agent, and/or between the surface and the binding agent), binding agents (e.g., an agent configured to bind to a capture agent, or a portion thereof, to facilitate immobilization of the capture agent to the surface), and/or capture agents to the surface.

In one non-limiting example, the capture agent can be a labeled protein, and the surface of the active area can include a linker that binds the label of the labeled protein. For instance, if the capture agent is a biotinylated antibody, then the surface can include a linker having an avidin (or a modified version of the avidin protein) that binds biotin. In another non-limiting example, the capture agent can be a labeled protein, and the surface includes a reactive layer configured to attach a binding agent that reacts with the capture agent. For instance, if the capture agent is a biotinylated antibody and the binding agent is an avidin, then the reactive layer can be an epoxide that reacts with amino groups present on avidin. In yet another instance, if the capture agent is an antibody, then the binding agent can be an immunoglobulin-binding protein (e.g., protein G, protein A, or protein L, as well as recombinant forms thereof, such as protein A/G) that binds to the Fab, L, and/or Fc regions of antibodies. In this instance, the binding agent can be directly attached to the surface (e.g., by way of physical adsorption) or indirectly attached by way of one or more reactive layers that attach to the binding agent.

To facilitate binding of the capture agents to the functionalized active area, any useful methodology and/or agent(s) can be employed. In one instance, the capture agent is physically adsorbed to the functionalized active area. In another instance, a covalent bond is present between the capture agent and a surface of the biosensor (e.g., a surface of the guide layer).

In yet another instance, a covalent bond is present between the capture agent and a binding agent, in which this binding agent in turn is attached directly or indirectly to the surface of the biosensor. The binding agent can include any useful compound, including linkers (e.g., any described herein), lipid layers (e.g., including bilipid layers having any useful lipophilic component, such as cholesterol), silanizing compounds (e.g., any described herein), and/or self-assembled monolayers (e.g., one or more thiols disposed on a metal (e.g., gold or silver) layer, in which this metal layer is disposed on the guide layer of the biosensor; and the one or more thiols can be functionalized to be attached to a capture agent). Any useful combination of linkers, capture agents, binding agents, and reactive layers can be employed to provide the functionalized active area.

Electronics Module

The electronics module can provide one or more electrical connections to the biosensor (e.g., the electrode region of the biosensor). In particular, the electronics module can include a portion (e.g., a recessed portion) configured to accommodate the biosensor, as well as include one or more electrical connections (e.g., pins, connectors, etc.) to the bond pad(s), contact pad(s), bond line(s), electrode(s), and reflector(s).

The electronics module can include any useful circuit components, such as an oscillator circuit (e.g., a Pierce circuit, a Colpitts circuit, or a Clapp circuit including an amplifier or a transistor, such as a bipolar junction transistor); one or more attenuation networks (e.g., including one or more circuit components to reduce the amplitude of a signal, such as by use of one or more resistors); one or more filters (e.g., a frequency selective, a high pass filter, a low pass filter, or a phase shifting filter); one or more amplifiers (e.g., transistors); one or more impedance matching networks (e.g., including one or more circuit components configured to match the impedance of the biosensor to another electronic component, in which exemplary impedance matching networks can include an inductor with an optional resistor in series with the non-grounded electrode(s) of the biosensor); and/or one or more coupling networks (e.g., configured to provide an output, such as a measured frequency shift).

FIG. 3A provides an exemplary circuit 300 for use in an electronics module. The circuit 300 can include an attenuation network 302, an amplifier 303, a resonator 304 (e.g., any biosensor described herein), a filter 305 (e.g., a frequency selective filter), a phase shift filter 306, and a coupling network 301, which provides an output 307 (e.g., a frequency shift output). The attenuation network 302, amplifier 303, resonator (biosensor) 304, and filter 305 (e.g., a low pass or high pass filter) can be employed to provide a feedback loop with sufficient gain to provide an oscillating circuit. In particular, the attenuation network 302 can be used to adjust the net gain of the feedback loop, and the filter 305 can be selected to maintain the desired frequency (or number of wavelength) required to provide an oscillation.

The feedback loop can include a phase shift filter 306 (or phase shifter) to ensure that the resonant frequency is determined at the point of 0° total phase. The coupling network 301 can include any useful component (e.g., an RF power divider, a direction coupler, an inductor, or a capacitor), which can be placed before or after the resonator 304 in order to provide an output 307. The coupling network 301, in turn, can be connected to a frequency counter and/or a computer in order to provide an output as a frequency shift.

Figure 3D:
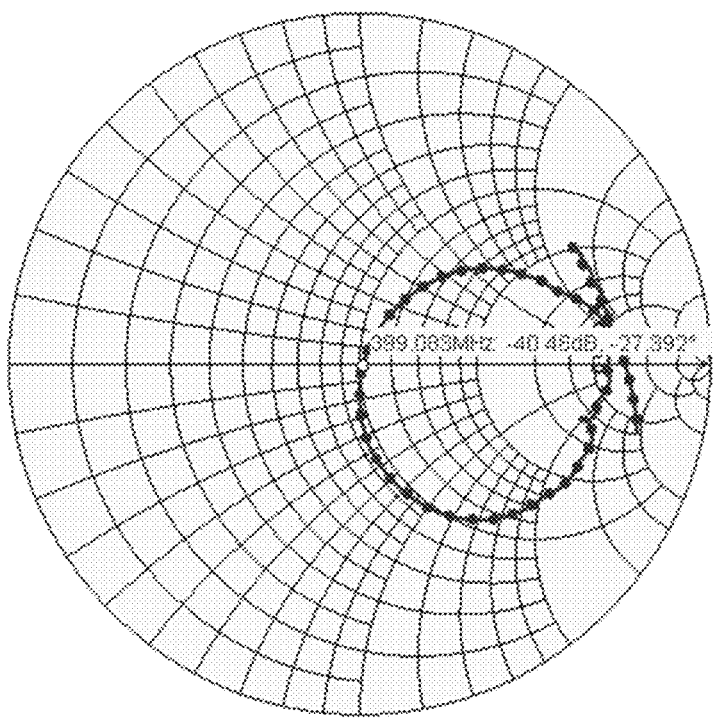

The circuit can include one or more impedance matching networks. For instance, FIG. 3B shows a circuit 310 that includes a first matching network 308 and an optional second matching network 309 in series with the resonator 304 (e.g., any biosensor described herein). As seen in FIG. 3C, any useful component can be used to form the matching network 320, including an inductor L1 in series with the resonator 304 and with an optional capacitor C1. Such impedance matching networks can be used to maximize power transfer to and from the biosensor, as well as to maximize the reflected signal. FIG. 3D shows impedance matching data for a matching network circuit (such as in FIG. 3C) used with a one-port biosensor.

A desired output (e.g., a frequency shift) can be measured in any useful manner, such as by employing a network analyzer or an oscillator circuit. Any useful oscillator circuit can be employed to detect the one or more outputs. Exemplary oscillator circuits include a Colpitts oscillator (e.g., for a one-port biosensor), a Pierce oscillator (e.g., for a two-port biosensor), a Clapp oscillator, a Hartley oscillator, etc.

Figure 3E:
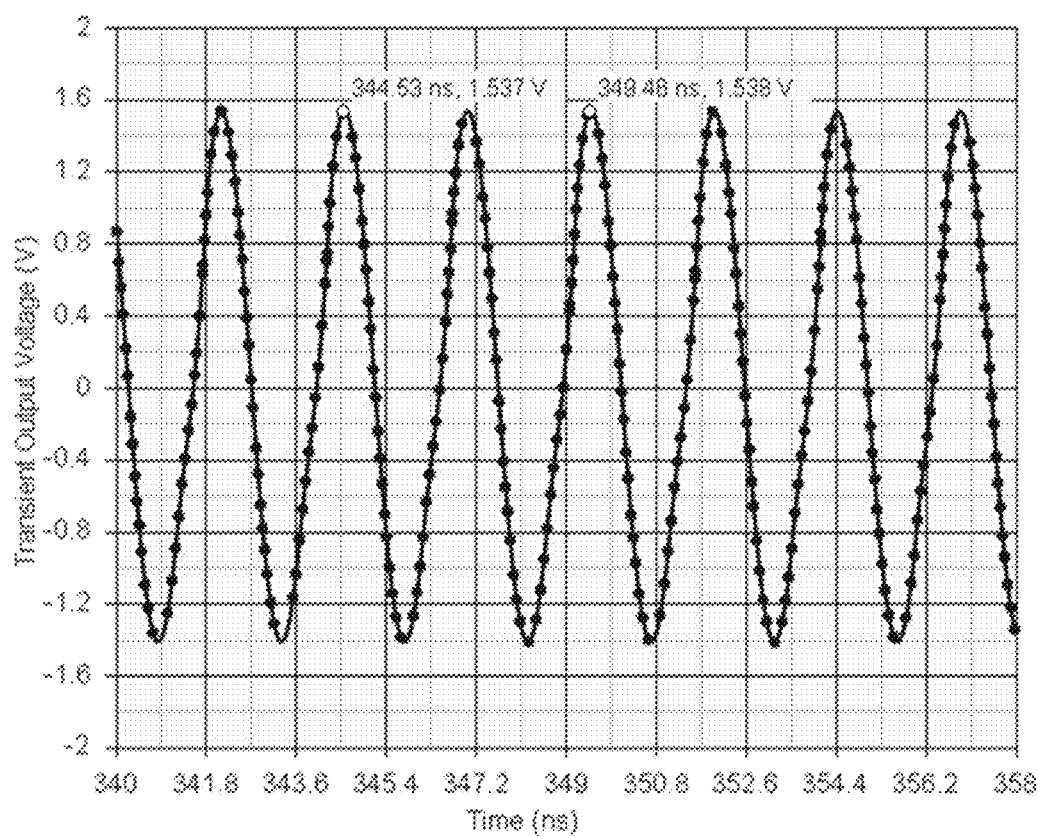
Figure 9:
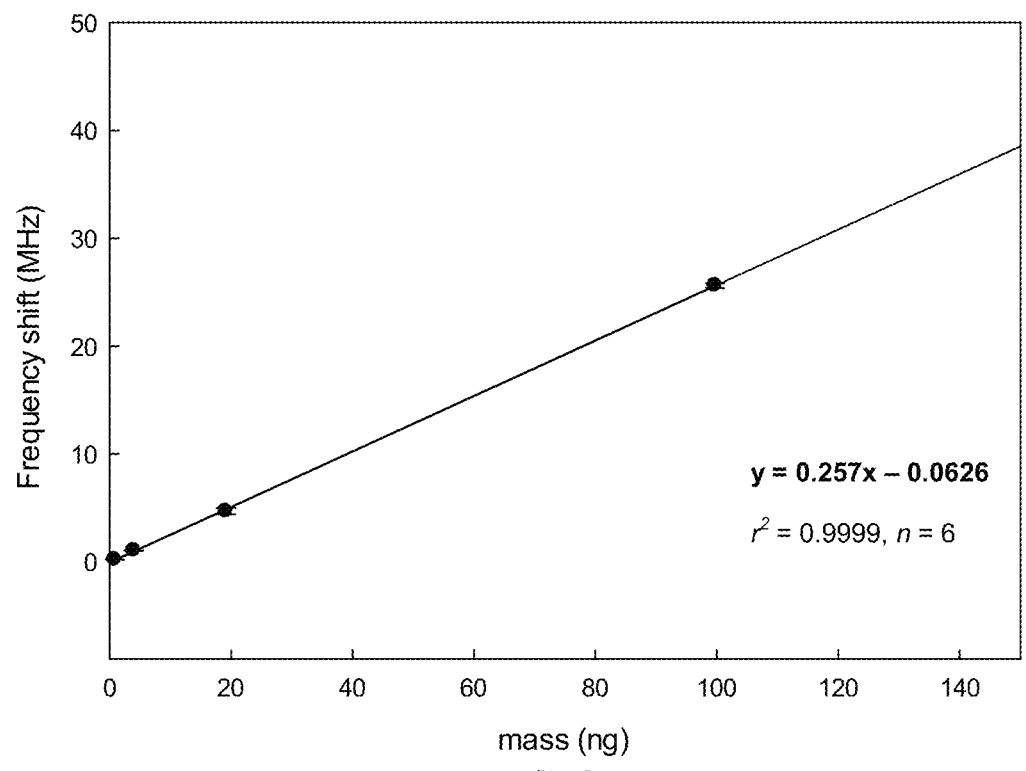
FIG. 9 is a graph showing the change in frequency shift for a particular mass of an analyte deposited on the biosensor surface.

In one instance, an output of the biosensor is connected to the gain device (e.g., an amplifier, such as a bipolar junction transistor), and the output of the gain device is connected to its input. In this way, an oscillating signal is established, which in turn can be used to resolve the resonant frequency shift of the biosensor. In use, a change in mass (resulting from binding a target) shifts the resonant frequency of the biosensor, and this shift in resonant frequency can be detected with an oscillator circuit. FIG. 3E shows transient data of a Colpitts oscillator employed to detect the output of a one-port biosensor. Such an oscillator circuit was employed to detect frequency shift per mass of deposited sample for a 400 MHz SH-SAW resonator (FIG. 9).

Each component in the circuit can be arranged in any useful manner. For instance, the circuit of FIG. 3A can be modified to include an attenuation network to be directly upstream of the resonator 304 and the amplifier 303 to be downstream of the resonator 304. Also, each component can be exchanged with any comparable replacement. Further, the phase shift filter 306 can be replaced with a variable phase shifter. Finally, one or more matching networks (e.g., as in FIG. 3B-3C) can be placed directly upstream and/or downstream of the resonator (biosensor).

Additional electronic components can include a frequency mixer, a frequency doubler, a frequency demultiplier, a frequency counter, a network analyzer, a capacitor, a transistor, etc., in which any components can be provided in any useful manner (e.g., as an integrated circuit). Other design considerations are described in Schmitt R F et al., "Rapid design of SAW oscillator electronics for sensor applications," *Sens. Actuat. B* 2001; 76:80-5; Martin S J et al., "Characterization of SH acoustic plate mode liquid sensors," *Sens. Actuat.* 1989; 20:253-68; and Grate J W et al., "Acoustic wave microsensors," *Anal. Chem.* 1993; 65(21):940A-8A, each of which is incorporated herein by reference in its entirety.

Fluidics Module

The fluidics module can include any useful port, via, chamber, and/or channel to deliver a sample to the functionalized active area of the biosensor. The fluidics module may be configured to be a disposable manifold that aligns with the biosensor and the electronics module. Alternatively, the fluidics module may be reusable for repeat use. The fluidics module can optionally include any useful microfluidic structure having a length, width, height, cross-sectional dimension, circumference, radius (e.g., external or internal radius), or diameter that is less than 1 mm. FIG. 4B provides an exemplary platform 4000 including a fluidics layer 4100 configured to be in fluidic communication with a functionalized active area 4200 of the biosensor. For instance, the fluidics layer 4100 can include a sample chamber 4150 designed to overlie the functionalized active area 4200.

Diagnostic Platform

The biosensor can be implemented in any useful platform, e.g., a diagnostic platform. The platform can include a power source (e.g., a portable power source), a control module (e.g., a personal digital assistant (PDA), a smart phone, a laptop, etc.), an electronics module (e.g., any described herein), and a fluidics module (e.g., any described herein). The platform can be configured to interface with any other useful component and, optionally, such components can be integrated into a portable sensor device.

Figure 7A:
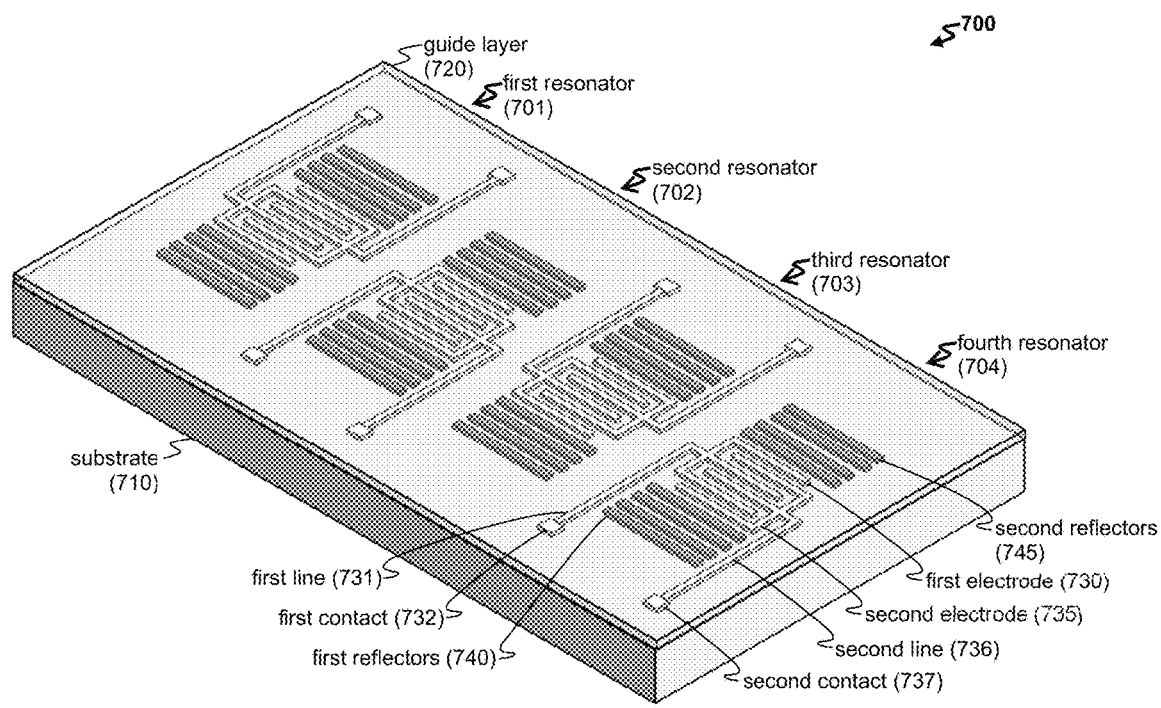
FIG. 7A-7B shows an exemplary array of biosensors. Provided are schematics of (A) a perspective view of an exemplary array 700 including four resonator biosensors and (B) a top view of another exemplary array 7000 with a plurality of resonators, contacts, and lines.

Optionally, the biosensor can be provided in an array format, in which a substrate includes more than one functionalized active area. In this way, the substrate can be configured to include multiple lanes, thereby allowing for the detection of multiple targets on the same biosensor or detecting the same target more than once for redundancy. FIG. 7A provides an exemplary biosensor 700 having a plurality of resonators 701,702,703,704 disposed on a single substrate 710, which in turn includes a guide layer 720. Each resonator includes its own functionalized active area disposed above the first and second electrodes 730,735. The regions of the first and second reflectors 740,745 are configured to provide the acoustic cavity in proximity to the overlapping area of the first and second electrodes 730,735. Each resonator can include one or more lines 731,736 and respective contacts 732,737 to provide appropriate electrical connections to the electrode region. Although the biosensor 700 provides a one-port configuration for each resonator, one or more of these resonators can be implemented in a two-port configuration.

Figure 7B:
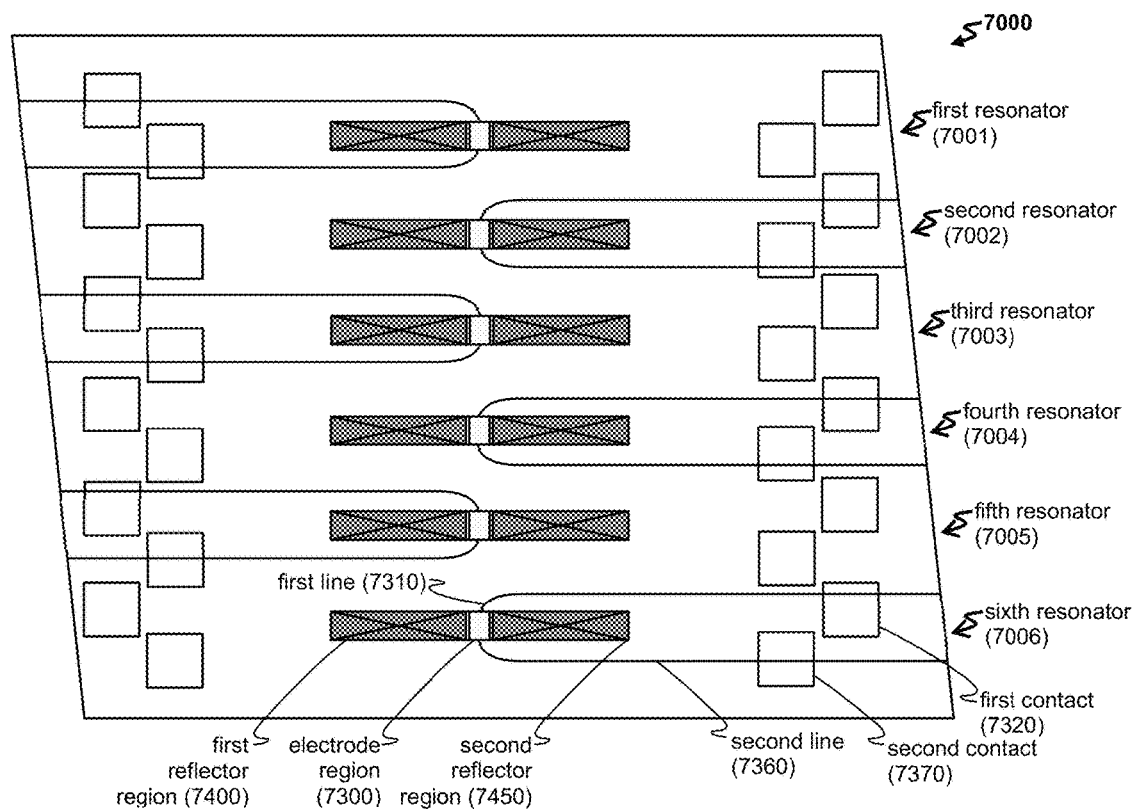
Figure 8:
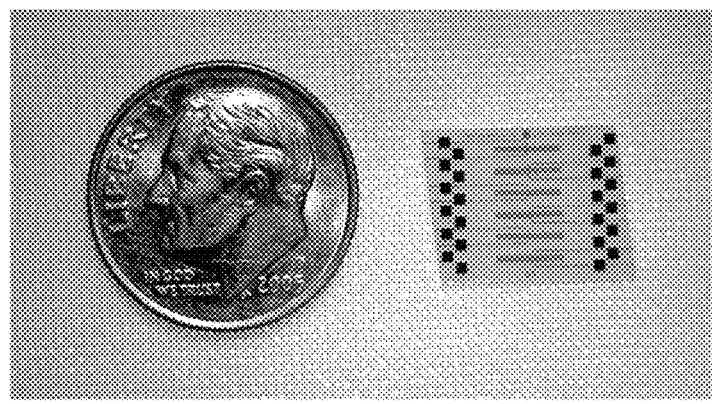
FIG. 8 is a picture of an exemplary array having six resonator biosensors.

Each component of the biosensor can be arranged in any useful manner. FIG. 7B provides an alternative design for a biosensor 7000 having six resonators 7001,7002,7003,7004, 7005,7006. Each resonator is configured to include an electrode region 7300 disposed between a first reflector region 7400 and a second reflector region 7450. The electrode region can include any useful number and configuration of electrodes or transducers. Each electrode region is connected to a first line 7310 and a second line 7360, which in turn are connected to a first contact 7320 and a second contact 7370, respectively. Such contacts can be configured to provide an electrical connection between the resonator and the electronic module of the platform. FIG. 8 provides a photograph of an exemplary biosensor design.

Capture Agents

Any useful capture agents can be used in combination in the present application. The capture agent can directly or indirectly bind the marker of interest. Further, multiple capture agents (e.g., optionally employed with one or more linkers and/or binding agents) can be used to bind the target and provide a detectable signal for such binding.

Exemplary capture agents include one or more of the following: a protein that binds to or detects one or more targets (e.g., an antibody including monoclonal or polyclonal forms thereof, an affibody, an enzyme, or fragments or recombinant forms of any of these), a globulin protein (e.g., bovine serum albumin), an amino acid, a peptide (e.g., a polypeptide, including modified forms thereof, such as glycosylated polypeptides or multimeric polypeptides), a polysaccharide (e.g., a cyclic polysaccharide), a nucleic acid (e.g., a nucleotide, a single stranded DNA, a single stranded RNA, and an oligonucleotide, including modified forms of any of these), a nanoparticle, a microparticle, a sandwich assay reagent, a label (e.g., one or more fluorescent labels, colorimetric labels, quantum dots, nanoparticles, microparticles, barcodes, radio labels (e.g., RF labels or barcodes), avidin, biotin, tags, dyes, an enzyme that can optionally include one or more linking agents and/or one or more dyes, as well as combinations thereof), a catalyst (e.g., that reacts with one or more targets), a lipid (e.g., a glycosylated lipid), and/or an enzyme (e.g., that reacts with one or more targets, such as any described herein). The capture agent can optionally include one or more labels, e.g., any described herein. In particular embodiments, more than one capture agent, optionally with one or more linking agents, can be used to detect a target of interest.

Optionally, linking agents can be used be attach the capture agent to the surface. Exemplary linking agents include compounds including one or more first functional groups, a linker, and one or more second functional groups. In some embodiments, the first functional group allows for linking between a surface and the linker (e.g., by way of a covalent or a non-covalent bond), and the second functional group allows for linking between the linker and the agent (e.g., a capture agent, a binding agent, a label, or any agent described herein, and by way of a covalent or a non-covalent bond). Exemplary linkers include any useful linker, such as polyethylene glycol (e.g., $(CH_2CH_2O)_{mg}$, where mg is from 1 to 50), an alkylene group (e.g., an optionally substituted $C_{1-12}$ alkylene or alkynyl chain), a heteroalkylene group, a carbocyclic ring (e.g., an aromatic ring, such as a phenyl group), a polypeptide (e.g., a dipeptide, tripeptide, etc.), and/or a flexible arm, e.g., 2, 3, 4, 5, 6, 7, 8, 9, 10, 11, 12, 13, 14, or 15 carbon atoms. The first and second functional groups can include any useful chemical moiety, such as moieties from a click-chemistry reaction pair selected from the group consisting of a Huisgen 1,3-dipolar cycloaddition reaction between an alkynyl group and an azido group to form a triazole-containing linker; a Diels-Alder reaction between a diene having a $4\pi$ electron system (e.g., an optionally substituted 1,3-unsaturated compound, such as optionally substituted 1,3-butadiene, 1-methoxy-3-trimethylsilyloxy-1,3-butadiene, cyclopentadiene, cyclohexadiene, or furan) and a dienophile or heterodienophile having a $2\pi$ electron system (e.g., an optionally substituted alkenyl group or an optionally substituted alkynyl group); a ring opening reaction with a nucleophile and a strained heterocyclyl electrophile; and a splint ligation reaction with a phosphorothioate group and an iodo group; and a reductive amination reaction with an aldehyde group and an amino group Other exemplary linkers include BS3 ([bis(sulfosuccinimidyl)suberate]; BS3 is a homobifunctional N-hydroxysuccinimide ester that targets accessible primary amines, such as those present on proteins or antibodies), NHS/EDC (N-hydroxysuccinimide and N-ethyl-(dimethylaminopropyl)carbodiimide; NHS/EDC allows for the conjugation of primary amine groups with carboxyl groups), sulfo-EMCS ([N-e-maleimidocaproic acid]hydrazide; sulfo-EMCS are heterobifunctional reactive groups (maleimide and NHS-ester) that are reactive toward sulfhydryl and amino groups), hydrazide (most proteins contain exposed carbohydrates and hydrazide is a useful reagent for linking carboxyl groups to primary amines), and SATA (N-succinimidyl-S-acetylthioacetate; SATA is reactive towards amines and adds protected sulfhydryls groups).

In particular embodiments, the linking agent is a silanizing compound. Exemplary silanizing agents include silazane (e.g., hexamethyldisilazane (HMDS)), haloalkylsilane (e.g., methyltrichlorosilane, trichlorocyclohexylsilane, dichlorodimethylsilane, dichloroethylsilane, bromotrimethylsilane, or chlorotrimethylsilane), haloarylsilane (e.g., fluorotriphenylsilane), trialkylsilylsilane (e.g., chlorotris(trimethylsilyl)silane), and silanol (e.g., 2-(trimethylsilyl)ethanol). Other silanizing agents include an agent having the structure of $(R^L)_3SiR^M$ or $R^LSi(R^M)_3$ or $R^LSi(SiR^M)_3$ or $(R^L)_2R^MSi$—L—$SiR^M(R^L)_2$, where each of $R^L$ is, independently, H, optionally substituted alkyl, hydroxyl, hydroxyalkyl, halo, haloalkyl, alkoxy, or aryl; each of $R^M$ is, independently, a functional moiety, such as optionally substituted alkyl, haloalkyl, hydroxyalkyl, alkenyl, alkoxy, aryl, alkaryl, heterocyclyl, heteroaryl, cycloalkyl, alkcycloalkyl, amino, aminoalkyl, or amido; L is a linker, such as optionally substituted alkylene, alkyleneoxy, arylene, heteroalkylene, heteroalkyleneoxy, or —N($R^{N1}$)—, where $R^{N1}$ is H, optionally substituted alkyl, alkaryl, or aryl; and where one of $R^L$ and X can optionally combine to form an optionally substituted heterocyclyl.

Such silanizing compounds can be used to graft an agent onto a surface (e.g., a silicon dioxide surface, or any surface including reactive hydroxyl groups). Other exemplary linking agents include pairs of linking agents that allow for binding between two different components. For instance, biotin and streptavidin react with each other to form a non-covalent bond, and this pair can be used to bind particular components.

Targets, Including Markers

The present device can be used to determine any useful targets or markers. Exemplary targets include a virus, a bacterium, a pathogen, a cell (e.g., a eukaryotic cell, a prokaryotic cell, a spore, as well as whole cells or fragments thereof), a protein (e.g., a prion, a membrane protein, a peptide marker, a hormone, etc.), a modified protein (e.g., a glycosylated, aminated, peglylated, phosphorylated, acetylated, truncated, or mutated protein), a peptide, a nucleic acid (including a nucleotide or a polynucleotide, e.g., DNA, RNA, mRNA, rTRNA, microRNA, etc. for detecting one or more alleles, pathogens, single nucleotide polymorphisms, mutations, etc.), a modified nucleic acid (e.g., a mutated nucleic acid), a cytokine (e.g., TNF-α, IL-12, or IL-1β), a prion, etc., as well as fragments or extracts of any of these. Additional targets, markers, and capture agents are described in U.S. Pat. No. 8,709,791, which is incorporated herein by reference in its entirety.

In some instances, the target includes a virus (e.g., animal, plant, fungal, and/or bacterial viruses), including Adenoviridae (e.g., adenovirus), Arenaviridae (e.g., Machupo virus), Astroviridae, Bunyaviridae (e.g., Hantavirus, Andes virus, Sin Nombre virus, and Rift Valley fever virus), Caliciviridae (e.g., Norwalk virus), Coronaviridae, Filoviridae (e.g., Ebola virus and Marburg virus), Flaviviridae (e.g., Japanese encephalitis virus, dengue virus, West Nile virus, and Yellow fever virus), Hepadnaviridae (e.g., hepatitis A virus, hepatitis B virus, and hepatitis C virus), Herpesviridae (e.g., Epstein-Barr virus and herpes simplex viruses, such as HSV-1 and HSV-2), Orthomyxoviridae (e.g., influenza viruses, such as influenza virus A (e.g., subtype H5N1, H3N2, or H1N1), influenza virus B, and influenza virus C), Papillomaviridae (e.g., human papilloma virus), Papovaviridae (e.g., papilloma viruses and polyomaviruses, such as Simian virus 40 (SV40)), Paramyxoviridae (e.g., respiratory syncytial virus, measles virus, mumps virus, and parainfluenza virus), Parvoviridae (e.g., adeno-associated virus), Picornaviridae (e.g., polioviruses, enteroviruses, rhinoviruses, hepatoviruses, and coxsackieviruses), Polyomaviridae, Poxviridae (e.g., variola viruses), Reoviridae (e.g., rotaviruses), Retroviridae (e.g., human T cell lymphotropic viruses (HTLV) and human immunodeficiency viruses (HIV), such as HIV-1 and HIV-2), Rhabdoviridae (e.g., rabies virus), and Togaviridae (e.g., encephalitis viruses and rubella virus).

Other exemplary targets include a bacterium, such as *Bacillus* (e.g., *B. anthracis*), Enterobacteriaceae (e.g., *Salmonella, Escherichia coli, Yersiniapestis, Klebsiella*, and *Shigella*), *Yersinia* (e.g., *Y. pestis* or *Y. enterocolitica*), *Staphylococcus* (e.g., *S. aureus*), *Streptococcus, Gonorrheae, Enterococcus* (e.g., *E. faecalis*), *Listeria* (e.g., *L. monocytogenes*), *Brucella* (e.g., *B. abortus, B. melitensis*, or *B. suis*), *Vibrio* (e.g., *V. cholerae*), *Corynebacterium diphtheria, Pseudomonas* (e.g., *P. pseudomallei* or *P. aeruginosa*), *Burkholderia* (e.g., *B. mallei* or *B. pseudomallei*), *Shigella* (e.g., *S. dysenteriae*), *Rickettsia* (e.g., *R. rickettsii, R. prowazekii*, or *R. typhi*), *Francisella tularensis, Chlamydia psittaci, Coxiella burnetii, Mycoplasma* (e.g., *M. mycoides*), etc.; allergens, such as peanut dust, mycotoxins, mold spores, or bacterial spores such as *Clostridium botulinum* and *C. perfringens* toxins, such as ricin, mycotoxin, tetrodotoxin, anthrax toxin, botulinum toxin, *staphylococcal* entertoxin B, or saxitoxin; a protozoon, such as *Cryptosporidium parvum, Encephalitozoa, Plasmodium, Toxoplasma gondii, Acanthamoeba, Entamoeba histolytica, Giardia lamblia, Trichomonas vaginalis, Leishmania*, or *Trypanosoma* (e.g., *T. brucei* and *T. Cruzi*); a helminth, such as cestodes (tapeworms), trematodes (flukes), or nematodes (roundworms, e.g., *Ascaris lumbricoides, Trichuris trichiura, Necator americanus*, or *Ancylostoma duodenale*); a parasite (e.g., any protozoa or helminths described herein); a fungus, such as *Aspergilli, Candidae, Coccidioides immitis*, and *Cryptococci*; an environmental contaminant; a water additive; an agricultural marker; a nucleic acid (e.g., oligonucleotides, polynucleotides, nucleotides, nucleosides, molecules of DNA, or molecules of RNA, including a chromosome, a plasmid, a viral genome, a primer, or a gene); a protein (e.g., a glycoprotein, a metalloprotein, an enzyme, a prion, or an immunoglobulin); a metabolite; a sugar; a lipid; a lipopolysaccharide; a salt; or an ion. Targets also include food-borne pathogens, such as *Salmonella* (e.g., *Salmonella Typhimurium*), pathogenic *E. coli* (e.g., O157:H7), *Bacillus* (e.g., *B. cereus*), *Clostridium botulinum, Listeria monocytogenes, Yersinia* (e.g., *Y. enterocolitica*), *Norovirus* (e.g., Norwalk virus), *Shigella, Staphylococcus aureus, Toxoplasma gondii, Vibrio* (e.g., *V. vulnificus, V. cholera, V. parahaemolyticus*), *Campylobacter jejuni*, and *Clostridium perfringens*; and weaponized pathogens, such as *Bacillus anthracis, Yersinia pestis, Francisella tularensis, Brucella* (e.g., *B. suis*), *Burkholderia mallei, Burkholderia pseudomallei, Shigella, Clostridium botulinum, Variola* (e.g., *V. major*), Filoviridae (e.g., Ebola virus and Marburg virus), Arenaviridae (e.g., Lassa virus and Machupo virus), *Clostridium perfringens*, any food-borne pathogen (e.g., *Salmonella* species, *Escherichia coli* O157:H7, or *Shigella*), *Chlamydia psittaci, Coxiella burnetii, Staphylococcal aureus, Rickettsia* (e.g., *R. prowazekii* or *R. rickettsii*), *Alphavirus* (e.g., Venezuelan equine encephalitis virus, eastern equine encephalitis virus, or western equine encephalitis virus), *Vibrio cholerae, Cryptosporidium parvum, Henipavirus* (e.g., Nipah virus), Bunyaviridae (e.g., Hantavirus or Rift Valley fever virus), Flaviviridae (e.g., Japanese encephalitis virus and Yellow fever virus), and *Coccidioides* spp.

Test Samples

The present device can be used to test any useful test sample, such as blood (e.g., whole blood), plasma, serum, transdermal fluid, interstitial fluid, sweat, intraocular fluid, vitreous humor, cerebrospinal fluid, extracellular fluid, lacrimal fluid, tear fluid, sputum, saliva, mucus, etc., and any other bodily fluid. The test sample can include any useful sample, such as a microorganism, a virus, a bacterium, a fungus, a parasite, a helminth, a protozoon, a cell, tissue, a fluid, a swab, a biological sample (e.g., blood, serum, plasma, saliva, etc.), an environmental sample, an agricultural sample, etc.

The sample can be obtained from any useful source, such as a subject (e.g., a human or non-human animal), a plant (e.g., an exudate or plant tissue, for any useful testing, such as for genomic and/or pathogen testing), an environment (e.g., a soil, air, and/or water sample), a chemical material, a biological material, or a manufactured product (e.g., such as a food or drug product).

Methods of Use

The present application also relates to methods of using a biosensor to detect any useful target. In one non-limiting example, the method includes use of a test sample requiring minimal or no sample preparation. In another non-limiting example, the method includes label-free detection of the target.

Figure 4A:
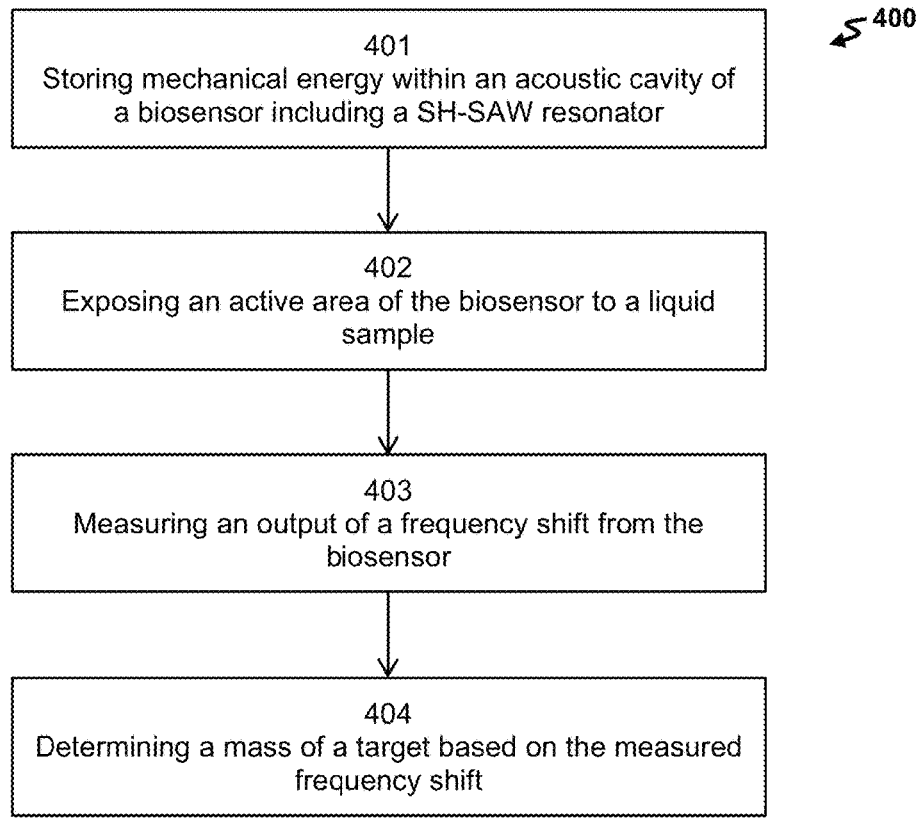
FIG. 4A-4B shows (A) an exemplary method 400 for detecting a target with a biosensor and (B) an exemplary platform 4000 for such detection.
Figure 4B:
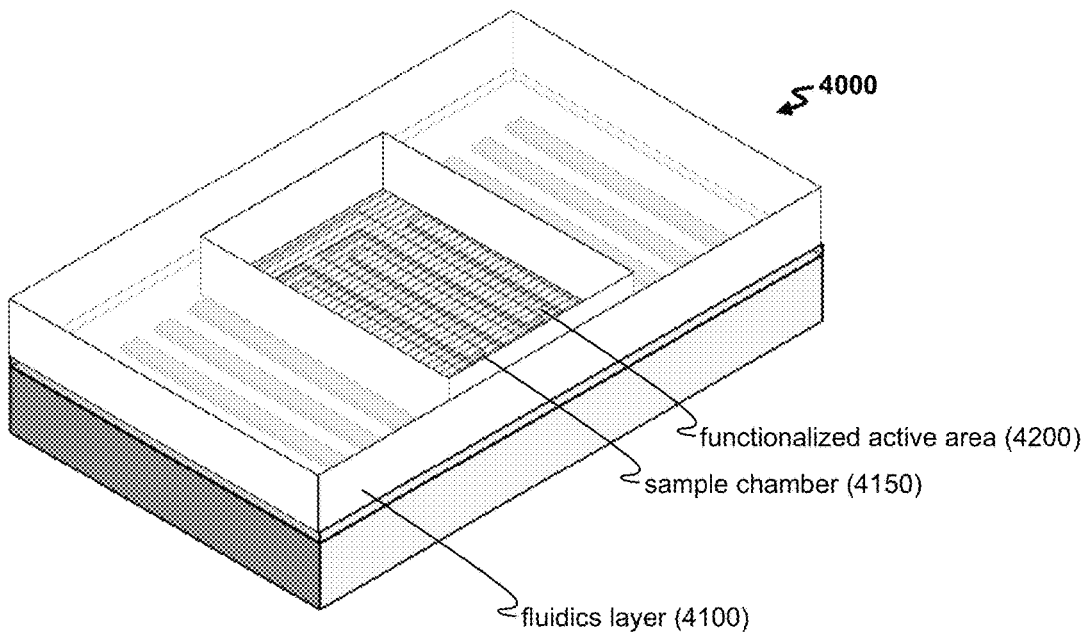

FIG. 4A provides an exemplary method 400 including the steps of storing 401 mechanical energy within an acoustic cavity of the biosensor, exposing 402 an area of the biosensor to a test sample, measuring 403 an output from the biosensor, and determining 404 a mass of a target based on the measured output. In the storing step 401, the biosensor can have any useful configuration described herein, such as any useful arrangement of electrode region(s) and reflector region(s), as well as any useful module (e.g., fluidic module and/or electronic module). In some embodiments, the biosensor is configured to be connected to an oscillator circuit to facilitate measurement of frequency shifts. In the exposing step 402, any useful sample (e.g., a liquid sample) can be tested with the biosensor. To detect the desired target, the sample can be delivered to an area of the biosensor, and this area can include one or more capture agents that specifically bind the desired target. The area (e.g., functionalized area) can be of any sufficient area to accommodate a minimized sample volume, while providing a large enough surface area to facilitate binding of multiple targets to the area (e.g., to increase sensitivity of the biosensor).

The measuring step 403 can include measuring any useful output (e.g., a shift in frequency), and the determining step 404 can include any useful methodology of correlating that output to a particular mass. In one instance, the methodology includes applying a determined extracted slope from a mass-frequency plot (a slope of df/dm) to the measured frequency shift (Δf), thereby determining the mass change (Δm).

EXAMPLES

Example 1: Fabrication of SH-SAW Resonator Arrays

Resonant-based Love wave sensors were fabricated using 36° YX lithium tantalate (LTO) wafers (Roditi Int'l Corp., London, UK) having a thickness of about 250-500 μm, a diameter of about 100 mm, and a single-side polished surface. Prior to metallization, wafers were cleaned in a barrel asher (PVA TePla AG, Asslar, Germany), followed by dipping in 1 vol. % hydrofluoric acid (HF).

A negative-tone photoresist (PR) AZ2020 (AZ Electronic Materials plc, Branchburg, N.J.) was applied onto the wafer using a spin coater with a Gyrset lid (Karl-Suss America, Inc., Waterbury Center, Vt.) to achieve a thickness of 2.0 μm. Wafers were metallized with 50 Å of titanium for improved adhesion, followed by deposition of 5000 Å aluminum using an electron-beam evaporator (Temescal, Wilmington, Mass.). An acetone bath was used to perform the lift-off, followed by rinsing in methanol, isopropyl alcohol, and de-ionized water. This was repeated for the metallization of the ground plane, bussing, and contact pads with the appropriate photomask.

The resonator included Bragg reflectors to create an acoustic standing wave, thereby defining an acoustic cavity. The Bragg reflector was composed of thin metal aluminum electrodes, which could be shorted or in an open configuration. The active acoustic cavity was about 300 μm×300 μm. Reflector regions were patterned with the appropriate photomask.

Silicon dioxide guide layers up to 5.0 μm in thickness were deposited onto the entire wafer using plasma enhanced chemical vapor deposition (PECVD) (Oerlikon Versaline, Pfäffikon, Switzerland). AZ4330 positive-tone PR (AZ Electronic Materials) was spin coated at 2000 rpm and 3000 rpm/sec. A PR mask was used to "open" the SiO$_2$ over the electrical contact pads. The SiO$_2$ was etched by RIE (Oerlikon Versaline). Each die had six resonator/sensors. Each die was 10×12 mm$^2$, yielding 44 die or 264 sensors per wafer.

Example 2: Mass Sensitivity of SH-SAW Resonator Arrays

A resonant shear-horizontal surface acoustic wave biosensor has been developed for monitoring biological capture events. The sensor included six identical channels operating at 400 MHz. The sensor was operated as either a one-port or two-port configuration. The one-port sensor offered slightly higher Q (~1000) than its counterpart. Passivation of the sensor was achieved using a thin layer of silicon dioxide (SiO$_2$). The silicon dioxide film was compatible with a variety of surface attachment chemistries, such as organosilane and self-assembled monolayers. The acoustic cavity (i.e., active area) of the sensor was, in one instance, about 0.1 mm$^2$ with low cross-talk between sensing elements. A sensitivity of 623 cm$^2 \cdot$g$^{-1}$ and detection limit of 0.2 pg were demonstrated.

The structure of the 400 MHz resonator in FIG. 7A shows a central acoustic cavity (electrode region 730) bounded by a pair of metal reflectors (first and second reflector regions 740,745). The entire surface was passivated with silicon dioxide to electrically isolate the structure from the liquid and enhance the mass sensitivity. The acoustic cavity had an area of about 0.1 mm$^2$, where biological capture layers were attached. At 400 MHz operating in water, the penetration depth of the acoustic wave was about 28 nm. The sensor was fabricated using a simple two-step mask process (e.g., as described in Example 1).

The mass sensitivity was measured by evaporating thin films of titanium onto the surface and measuring the corresponding frequency shift. Mass sensitivity S$^f_m$[m$^2 \cdot$g$^{-1}$] was defined as follows:

$$S^f_m = \frac{1}{f_O} \frac{df}{dm} A, \quad \text{(Eq. 1)}$$

where f$_O$ [Hz] is the operating frequency, df/dm [Hz·g$^{-1}$] is the extracted slope from a mass-frequency plot, and A [m$^2$] is the area of the sensor. In FIG. 9, the measured frequency shift versus applied mass revealed a slope of 0.257 MHz·ng$^{-1}$. Using the area of the cavity (e.g., 0.097 mm$^2$), the sensitivity S$^f_m$ was computed to be 623 cm$^2 \cdot$g$^{-1}$. In typical frequency measurements, the resolution is 10 Hz with a network analyzer. The detection limit was defined as follows:

$$DL_m = \frac{5 \times N \times A}{S \times f_O}, \quad \text{(Eq. 2)}$$

where N[Hz] is the noise level, A[m$^2$] is the area, S[m$^2 \cdot$g$^{-1}$] is the sensitivity, and f$_O$ [Hz] is the center frequency. The factor of 5 defines resolving the signal above the noise floor. Using Equation 2, it was determined that the mass sensitivity was about 0.2 pg or about 100 times more sensitive than the 325 MHz delay line SH-SAW.

In practical applications, an oscillator can be implemented to reduce power consumption and permit operation of a large number of sensors through switching. In addition, the oscillator can be used to increase the frequency resolution to about 0.1 Hz. A Colpitts oscillator circuit was developed around a low noise NPN transistor to provide a sustained frequency output. The start-up time was 20 ns with a second harmonic that was over 24 dB down from the primary oscillation frequency. Further enhancements can be made to improve the dynamic range of oscillation due to operating in aqueous environments.

A SH-SAW resonator has been developed with a sensitivity and detection limit that exceeds existing delay-line acoustic sensors. In particular, the resonator employs a standing wave that undertakes multiple passes within the acoustic cavity, and this standing wave exhibits enhanced sensitivity to mass changes at the surface of the piezoelectric substrate. The size of this acoustic cavity can be minimized to reduce sample use (e.g., a sample volume of less than about 50 nL), and the size of the sensor can be minimized to provide a plurality of sensors per die (e.g., of from about 5 to 10 sensors per 1 $cm^2$ die). In addition, the sensor can be configured to have multiple sensing channels and can be scaled to suit specific applications.

The SH-SAW resonator also provides a more useful output metric. For instance, the change in resonant frequency upon binding to the target (a frequency shift) is a useful output metric that does not exhibit phase wrapping. In addition, circuitry for frequency detection can be compact (e.g., a monitoring oscillator circuit or a compact frequency sweep circuit).

It avoids the problem of phase-tracking which is problematic in delay-line based detection sensors. It also reduces the material requirements to conjugate and operate the sensor, especially when costly biological agents are required. Further improvements to boost sensitivity include using active capture of targets, increasing the thickness of the guide layer, and/or increasing the operating frequency.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A biosensor comprising:
   a piezoelectric substrate comprising a top surface;
   an electrode region disposed on the top surface of the piezoelectric substrate, wherein the electrode region is configured to launch a shear horizontal surface acoustic wave and to detect the acoustic wave transmitted through the substrate;
   one or more reflector regions disposed on the top surface of the piezoelectric substrate and disposed outside of a periphery of the electrode region, wherein the one or more reflector regions are configured to provide an acoustic cavity disposed within the piezoelectric substrate, and wherein the acoustic cavity is configured to store mechanical energy from the acoustic wave;
   a guide layer overlying the top surface of the piezoelectric substrate, the electrode region, and the one or more reflector regions, or portions thereof, in which a shear velocity in the guide layer is less than a shear velocity in the piezoelectric substrate; and
   a functionalized active area disposed in proximity to the acoustic cavity and comprising one or more capture agents configured to bind one or more targets.

2. The biosensor of claim 1, wherein binding of the one or more targets to the one or more capture agents configured to result in a frequency, phase, or amplitude shift of the acoustic wave as a function of the mass of bound one or more targets.

3. The biosensor of claim 2, where the frequency shift is of from about 0.1 MHz/ng to about 2 MHz/ng.

4. The biosensor of claim 1, wherein the biosensor is configured as a one-port device.

5. The biosensor of claim 1, wherein the electrode region comprises a pair of a transmitting transducer and a receiving transducer, the electrode region is configured to propagate the acoustic wave in a first direction, and the electrode region has a first edge and a second edge in which the first and second edges are parallel to each other and are perpendicular to the first direction;
   wherein the one or more reflectors regions comprises a first reflector disposed in proximity to the first edge and a second reflector disposed in proximity to the second edge; and
   wherein the functionalized active area is disposed above the pair of transducers.

6. The biosensor of claim 1, wherein the biosensor is configured as a two-port device.

7. The biosensor of claim 6, wherein the electrode region comprises a first pair of transducers and a second pair of transducers, the electrode region is configured to propagate the acoustic wave in a first direction, and a spacing separates the first and second pairs of transducers, wherein the spacing is dimensioned to be parallel to the first direction;
   wherein the one or more reflectors regions comprises a first reflector disposed in proximity to the first pair and a second reflector disposed in proximity to the second pair; and
   wherein the functionalized active area is disposed above the spacing and between the first and second pairs of transducers.

8. The biosensor of claim 1, wherein the piezoelectric substrate comprises lithium tantalate, lithium niobate, potassium niobate, quartz, langatate, langasite, langanite, or a combination thereof.

9. The biosensor of claim 8, wherein the guide layer comprising a polymer, an oxide, a dielectric, or a combination thereof.

10. The biosensor of claim 1, wherein the functionalized active area has an area of from about 0.01 $mm^2$ to about 10 $mm^2$.

11. The biosensor of claim 10, wherein the one or more capture agents are disposed on a surface of the functionalized active area.

12. The biosensor of claim 10, wherein the functionalized active area is configured to contact a sample volume of from about 0.5 nL to about 100 nL.

13. The biosensor of claim 1, further comprising:
a fluidics layer comprising a sample chamber configured to overlie the functionalized active area.

14. The biosensor of claim 13, further comprising:
one or more electrical lines connected to the electrode region; and
one or more electrical contacts connected to the one or more electrical lines.

15. The biosensor of claim 1, wherein the biosensor is configured to operate at a frequency of from about 80 MHz to about 2.5 GHz.

16. An array comprising a plurality of biosensors of claim 1, wherein each biosensor can be the same or different.

17. A biosensing platform comprising:
a Love wave biosensor of claim 1; and
a fluidics layer configured to be in fluidic communication with the functionalized active area of the biosensor.

18. The biosensing platform of claim 17, wherein the fluidics layer further comprises a sample chamber configured to overlie the functionalized active area.

19. The biosensing platform of claim 17, further comprising a matching network in series with the biosensor.

20. The biosensing platform of claim 17, further comprising:
an attenuation network configured to attenuate a first input signal and to transmit an attenuated input signal;
an amplifier configured to amplify the attenuated input signal and to provide an amplified signal, wherein the amplified signal is transmitted to the biosensor as a second input signal; and
a filter configured to receive an output signal from the biosensor, thereby providing a filtered signal.

21. A method for detecting one or more targets, the method comprising:
storing mechanical energy within an acoustic cavity disposed within a biosensor, wherein the biosensor is configured to launch a shear horizontal surface acoustic wave that provides the mechanical energy;
exposing a functionalized active area of the biosensor to a liquid sample or a gas, wherein the functionalized active area is disposed above the acoustic cavity and comprises one or more capture agents configured to bind one or more targets;
measuring an output of a frequency shift or an amplitude change from the biosensor; and
determining a mass of the one or more targets based on the measured frequency shift.

22. The method of claim 21, further comprising, prior to the storing step,
providing an oscillating input signal to the biosensor.

23. The method of claim 21, wherein the liquid sample comprises whole blood, plasma, serum, sputum, cerebrospinal fluid, tear fluid, interstitial fluid, a biological sample, an environmental sample, or an agricultural sample.

24. The method of claim 21, wherein the liquid sample comprises one or more viruses, pathogens, whole cells, bacteria, proteins, nucleic acids, toxins, peptides, biomarkers, and/or cytokines.

25. The method of claim 21, wherein the exposing step further comprises delivering the liquid sample to a sample chamber in fluidic communication with the functionalized active area of the biosensor.

* * * * *